(12) United States Patent
Farshi et al.

(10) Patent No.: US 12,090,483 B2
(45) Date of Patent: Sep. 17, 2024

(54) DIAGNOSTIC SAMPLE COLLECTION SYSTEM

(71) Applicant: Amazon Technologies, Inc., Seattle, WA (US)

(72) Inventors: Jasmin B. Farshi, San Jose, CA (US); Pan Zhang, San Jose, CA (US); Jonathan Barry Hirst, Sunnyvale, CA (US); Babak Ziaie, West Lafayette, IN (US); Bela Incze, Morgan Hill, CA (US); Babar M. Koraishy, Livermore, CA (US)

(73) Assignee: Amazon Technologies, Inc., Seattle, WA (US)

( * ) Notice: Subject to any disclaimer, the term of this patent is extended or adjusted under 35 U.S.C. 154(b) by 0 days.

(21) Appl. No.: 17/703,570

(22) Filed: Mar. 24, 2022

(65) Prior Publication Data
US 2023/0115746 A1   Apr. 13, 2023

Related U.S. Application Data

(60) Provisional application No. 63/254,656, filed on Oct. 12, 2021.

(51) Int. Cl.
*C12Q 1/686* (2018.01)
*B01L 1/00* (2006.01)
(Continued)

(52) U.S. Cl.
CPC .............. *B01L 3/5029* (2013.01); *B01L 1/50* (2013.01); *B01L 3/5025* (2013.01);
(Continued)

(58) Field of Classification Search
CPC .... B01L 3/5029; B01L 2200/10; C12Q 1/686
See application file for complete search history.

(56) References Cited

U.S. PATENT DOCUMENTS

| 9,446,418 B2 | 9/2016 | Johns et al. |
| 11,131,000 B1 | 9/2021 | Lahoud et al. |
| (Continued) | | |

FOREIGN PATENT DOCUMENTS

| EP | 2743704 A2 | 6/2014 |
| EP | 3394293 B1 | 5/2021 |

OTHER PUBLICATIONS

PCT, "International Search Report and Written Opinion" Application No. PCT/US2022/077921, mailed Jan. 25, 2023, 19 pages.

*Primary Examiner* — Young J Kim
(74) *Attorney, Agent, or Firm* — Eversheds Sutherland (US) LLP

(57) ABSTRACT

Systems, methods, and collection devices are disclosed for rapid, local PCR testing. The PCR testing system may be configured for use with a disposable sample collection device that includes a swab configured for collecting a biological sample from a patient; and a sample container configured to receive the swab and separate a bulk quantity of the biological sample from the swab for containment in a bulk collection chamber, which is located with the sample container, wherein the sample container is configured to meter a selected volume of the biological sample into a PCR sample tube, which contains a lyophilized master mix, releasably attachable to the sample container.

19 Claims, 19 Drawing Sheets

(51) Int. Cl.
  *B01L 3/00*        (2006.01)
  *B01L 7/00*        (2006.01)
  *G01N 33/487*      (2006.01)
  *G16H 10/40*       (2018.01)
  *G16H 40/40*       (2018.01)

(52) U.S. Cl.
  CPC ...... *B01L 7/5255* (2013.01); *G01N 33/48771* (2013.01); *G01N 33/48792* (2013.01); *G16H 10/40* (2018.01); *G16H 40/40* (2018.01); *B01L 2200/04* (2013.01); *B01L 2200/0689* (2013.01); *B01L 2200/082* (2013.01); *B01L 2200/10* (2013.01); *B01L 2200/16* (2013.01); *B01L 2300/021* (2013.01); *B01L 2300/027* (2013.01); *B01L 2300/044* (2013.01); *B01L 2300/0609* (2013.01); *B01L 2300/0654* (2013.01); *B01L 2300/0681* (2013.01); *B01L 2300/0832* (2013.01); *B01L 2300/1805* (2013.01); *B01L 2300/1894* (2013.01); *B01L 2400/0478* (2013.01); *C12Q 1/686* (2013.01)

(56) References Cited

U.S. PATENT DOCUMENTS

| | | |
|---|---|---|
| 2002/0013224 A1 | 9/2002 | Li-Sucholeiki |
| 2006/0011162 A1 | 5/2006 | Squilla et al. |
| 2006/0024649 A1 | 11/2006 | Jensen et al. |
| 2010/0323343 A1* | 12/2010 | Egan .................... G01N 33/558 435/5 |
| 2011/0256531 A1* | 10/2011 | Rajagopal ................ C12Q 1/04 435/7.1 |
| 2016/0258849 A1* | 9/2016 | Murayama .............. B01L 3/502 |
| 2020/0278368 A1* | 9/2020 | Hopper .............. G01N 35/1009 |
| 2021/0028597 A1 | 9/2021 | Tu et al. |
| 2021/0366607 A1 | 11/2021 | Kolluri et al. |
| 2021/0407692 A1 | 12/2021 | Wohlstadter et al. |

* cited by examiner

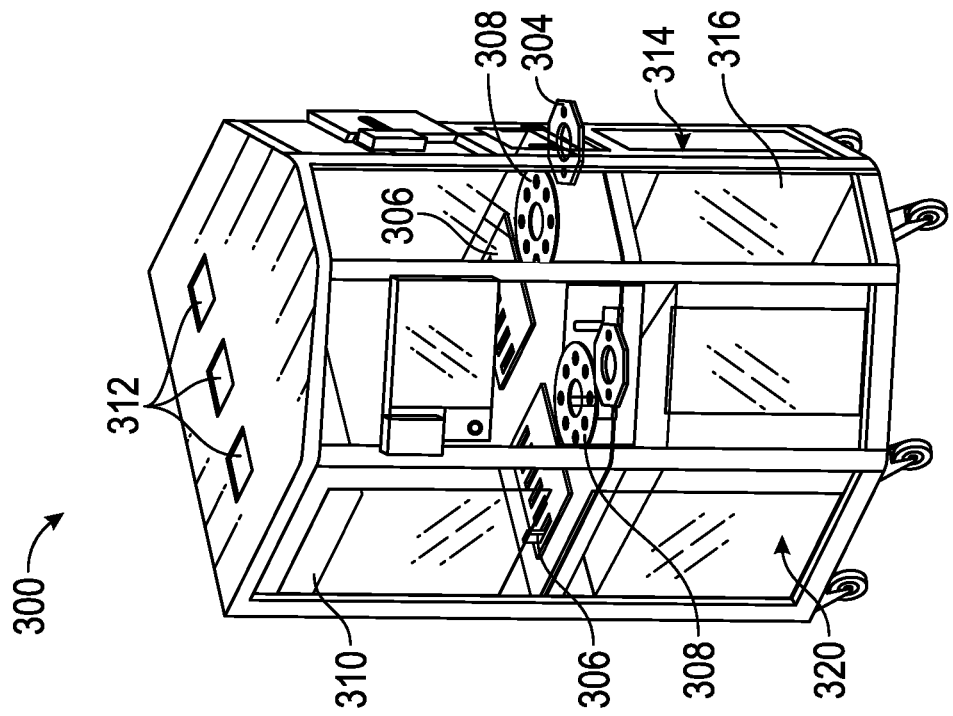
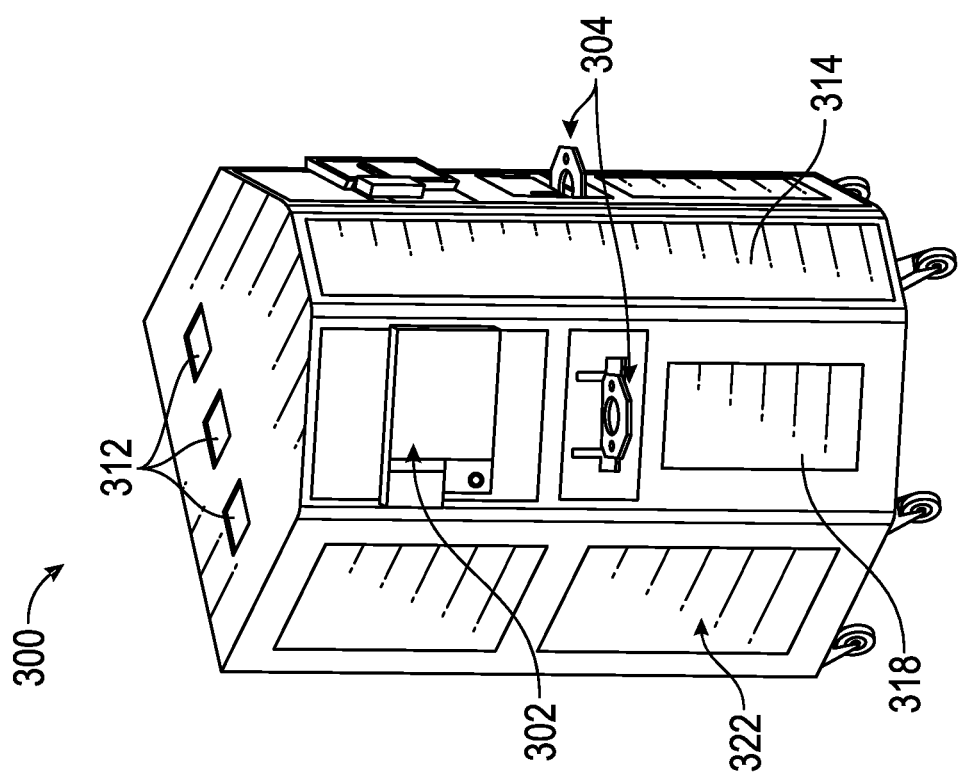
FIG. 3B
FIG. 3A

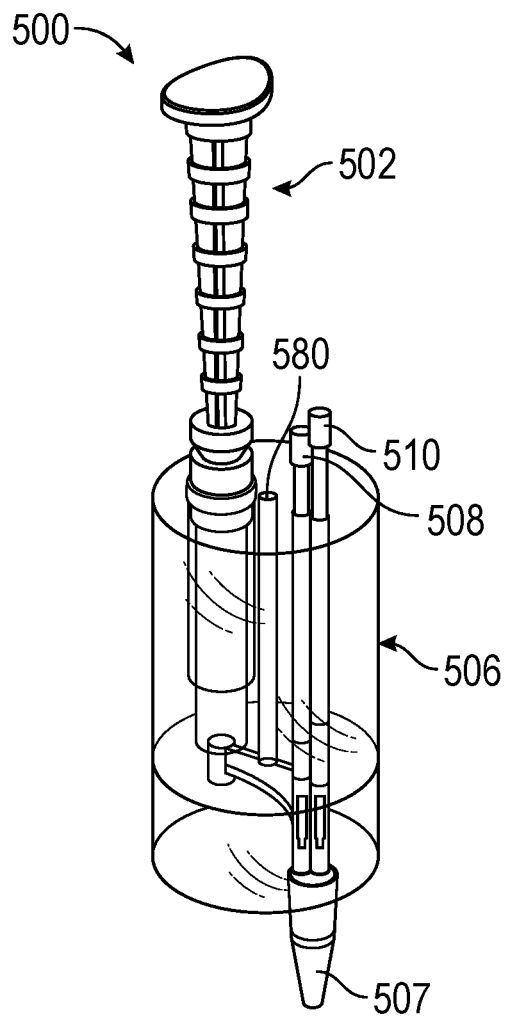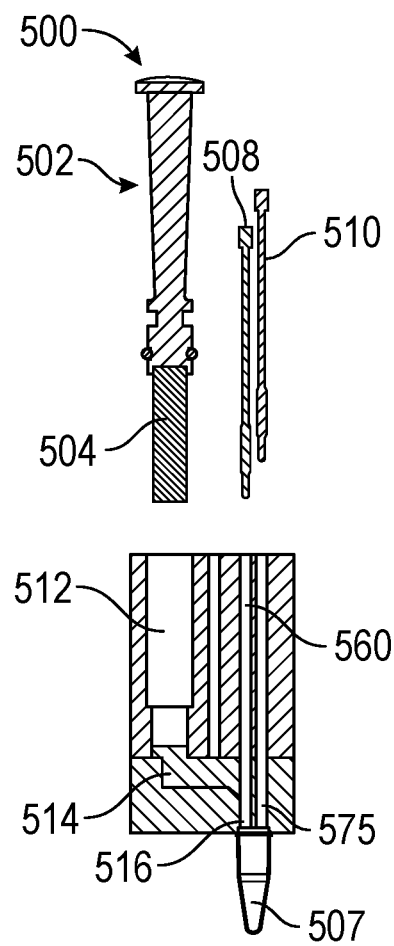
FIG. 5C
FIG. 5D

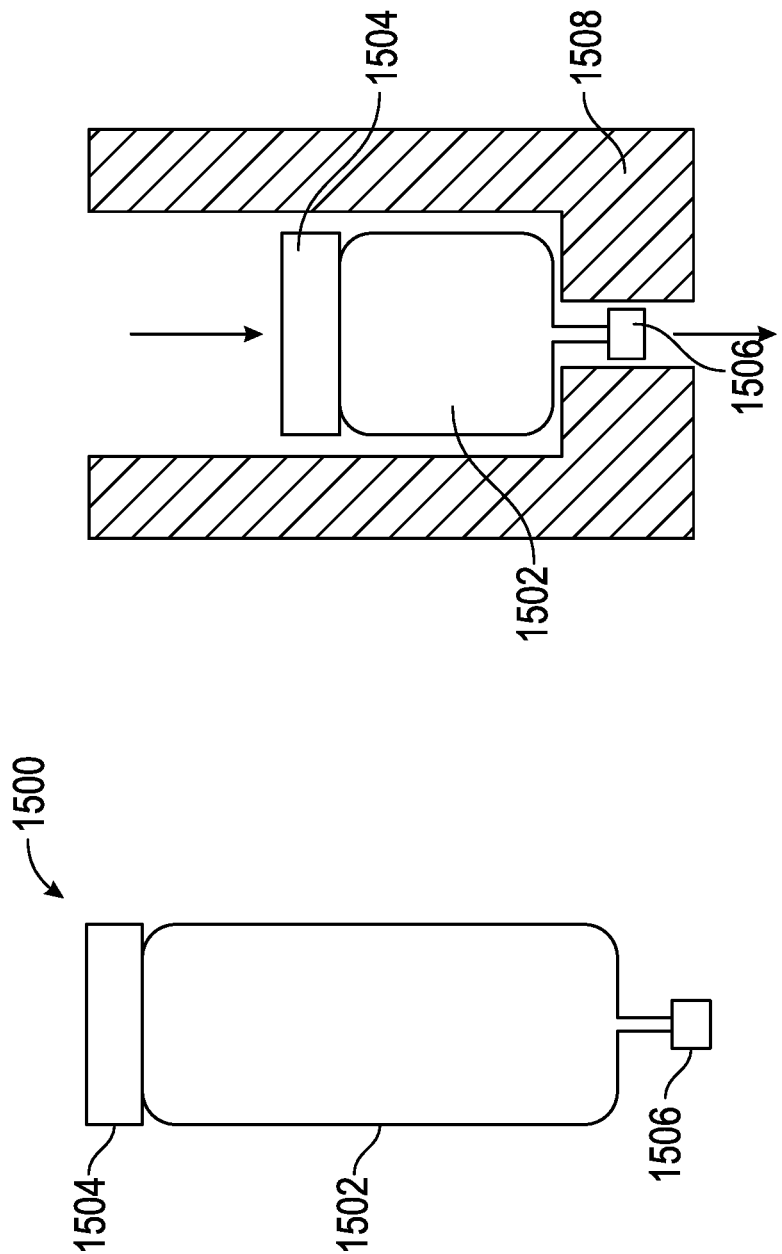

DIAGNOSTIC SAMPLE COLLECTION SYSTEM

CROSS-REFERENCE TO RELATED APPLICATION(S)

This application claims priority to U.S. Provisional Application No. 63/254,656, filed Oct. 12, 2021, the content of which is incorporated herein by reference in its entirety.

BACKGROUND

PCR (polymerase chain reaction) diagnostic testing for various illnesses may be desirable for a number of reasons. Typical PCR tests (e.g., for COVID-19 testing) require that a sample be collected from a person via a nasal swab or saliva, and then the collected sample is transported to a lab, where the sample is processed and placed into a 96-well plate for high volume PCR testing. However, such PCR testing may be cumbersome, time consuming, and require a centralized lab setup. Systems and methods for rapid PCR testing at a local (e.g., point of care) site may therefore be desired.

BRIEF DESCRIPTION OF THE DRAWINGS

FIGS. 3A-3B are perspective views of an example testing module for localized diagnostic testing used in conjunction with a SCD as described herein.

FIG. 5C is a transparent, perspective view of an example SCD, according to one embodiment of the present disclosure.

FIG. 5D is cross-sectional, exploded view of an example SCD, according to one embodiment of the present disclosure.

FIGS. 6A-6B depict an example nasal SCD, according to one embodiment of the present disclosure.

Figure 1A:
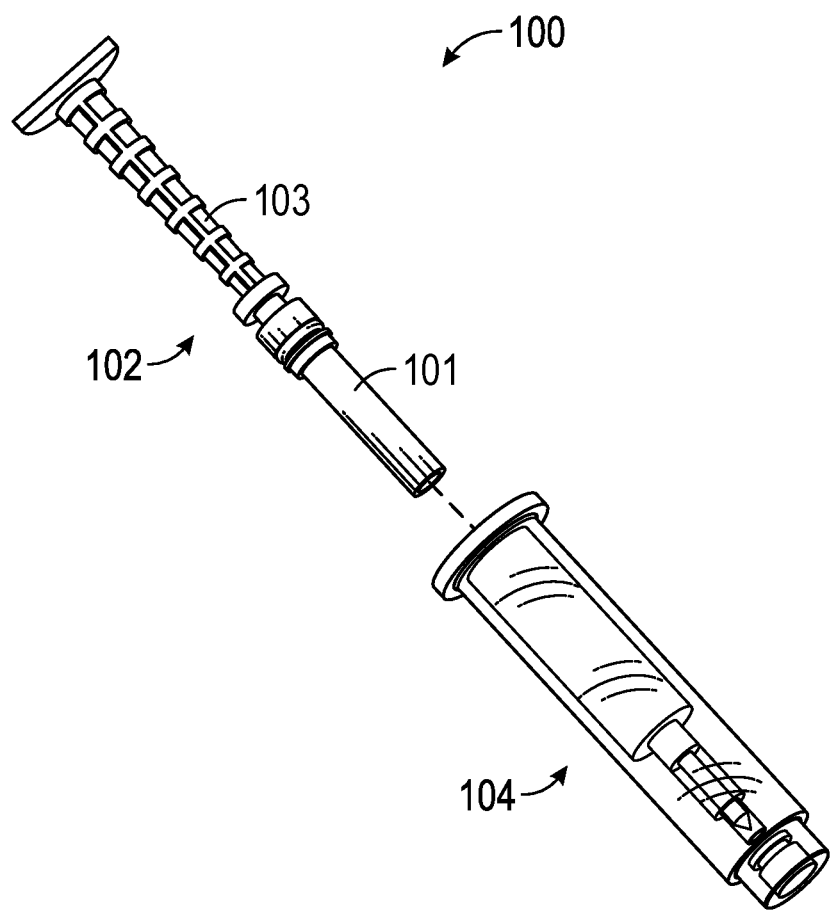
FIG. 1A is perspective view of an example sample collection device (SCD) according to one embodiment of the present disclosure.

The detailed description is set forth with reference to the accompanying drawings. The drawings are provided for purposes of illustration only and merely depict example embodiments of the disclosure. The drawings are provided to facilitate understanding of the disclosure and shall not be deemed to limit the breadth, scope, or applicability of the disclosure. The use of the same reference numerals indicates similar, but not necessarily the same or identical components. Different reference numerals may be used to identify similar components. Various embodiments may utilize elements or components other than those illustrated in the drawings, and some elements and/or components may not be present in various embodiments. The use of singular terminology to describe a component or element may, depending on the context, encompass a plural number of such components or elements and vice versa.

DETAILED DESCRIPTION

Overview

Embodiments of the present disclosure include systems and methods for rapid, local PCR testing. To facilitate this, sample collection devices (SCDs) configured for use in these systems and methods have been developed.

In particular embodiments, the SCDs are used to collect and transfer a biological specimen from a patient and into a PCR sample tube for subsequent PCR testing. In embodiments, the SCDs are configured to be used in connection with a local testing module. The PCR sample tube comprises a master mix as known in the art. As used herein, the term "lyophilized master mix" includes one or more suitable chemical agents, such as lysates, for facilitating PCR testing as known in the art, which may be in a lyophilized or otherwise dried form, such as a powder. The master mix may be rehydrated upon contact with an aqueous biological sample, optionally with additional water supplied within the testing module and/or sample collection device. The sample tube may be a standard size 0.2 mL tube. It is not necessary to use a standard size tube; however, standard size tubes may be cheaper to procure and easier to process.

In some embodiments, the SCD is configured for collecting saliva specimen from the mouth of a human, or for collecting a nasal mid-turbinate (NMT) specimen, or anterior nasal specimen, from a nostril of a human. These collections may be self-administered by a patient following collection instructions. In some embodiments, the SCD is configured for collecting a nasopharyngeal specimen (NP) or oropharyngeal (OP) (throat) specimen, performed by a trained healthcare provider. In other embodiments, the sample collection device may be configured for collecting other biological fluids from a human or non-human mammals. The collected specimen may be referred to herein as a "sample". The patient may be a human. The sample may also be collected from an object.

In embodiments, the sample collection device may include a swab configured to hold a biological sample, and a sample container configured to receive the swab and enable transfer of a first portion of the biological sample to a first chamber of the sample container, wherein the sample container is configured to enable transfer of a second portion of the biological sample from the first chamber into a PCR sample tube that is releasably attached to the sample container.

In some embodiments, the SCD may include a swab stick configured for collecting a biological fluid sample from a patient; and a sample container configured to receive the swab stick and separate a bulk quantity of the biological fluid sample from the swab stick for containment in a bulk collection chamber for lysing, which is located within the sample container. The sample container is configured to meter a selected volume of the lysed biological fluid sample into a PCR sample tube, which contains a lyophilized master mix, releasably attachable to the sample container. In particular embodiments, the swab stick is configured for collection of a saliva specimen from a patient or is configured for collection of a nasal or throat surface specimen from a patient.

The overall size of the SCD may be about the size of a standard syringe. For example, the SCD may be about 20 mm to about 30 mm wide and about 100 mm to about 150 mm long when the swab stick is fully inserted into the sample container.

In some particular embodiments, the swab stick comprises an absorbent swab material, and the sample container and the swab stick are configured to engage with one another to compress the absorbent swab material to release a collected biological specimen, e.g., a biological fluid sample into a bulk collection chamber within the sample container.

The swab stick may include a handle end portion, an opposing end portion which includes the absorbent swab material, and a sealing member disposed between the handle end portion and the absorbent swab material, wherein the sealing member is configured to matingly engage with an interior surface of a swab receiving chamber in the sample container.

The sample container may include an elongated cylindrical body having a first end opening for receiving the absorbent swab material end portion of the swab stick, and an opposed second end configured for releasably attaching to a PCR sample tube. In some embodiments, a sealed PCR sample tube is attached to the second end of the sample container, wherein the PCR sample tube has a foil seal covering a lyophilized master mix contained within the PCR sample tube. In some embodiments, the sample container further includes a water chamber, which contains water, and a water chamber piston, which is configured to pierce the foil seal and to transfer the water into the PCR sample tube.

In some embodiments, the sample container further includes a micro sample chamber in fluid communication with the bulk collection chamber, wherein the micro sample chamber is configured to hold a select volume, e.g., 5 µl, of the lysed biological fluid sample.

In some embodiments, the sample container further includes a metering piston configured to be translated within the bulk collection chamber and meter a selected volume of the lysed biological fluid sample into an attached PCR sample tube.

In some particular embodiments, the SCD for use in PCR testing includes (i) a swab stick which has a plunger handle and a saliva swab extending from the plunger handle; and (ii) a sample container configured to receive the saliva swab therein following collection of a saliva specimen. The sample container has (a) a swab chamber for receiving the saliva swab; (b) a bulk saliva collection chamber in fluid communication with the swab chamber, the bulk saliva collection chamber being configured to receive saliva transferred from saliva swab; (c) a micro sample chamber in fluid communication with the bulk saliva collection chamber, the micro sample chamber being configured to hold a selected volume of the saliva transferred from the bulk saliva collection chamber; and (d) a metering piston with a piercing tip. The sample container is configured to (i) releasably attach to a PCR sample tube, which contains a lyophilized master mix, (ii) pierce a seal on the PCR sample tube, and (iii) to meter the selected volume of the saliva from the micro sample chamber into the PCR sample tube.

In embodiments, the SCD includes at least a swab and a sample container. In some embodiments, the SCD provided to a testing module may include an attached PCR sample tube. For example, the SCD provided to the patient for receiving the biological specimen may include a SCD having a pre-attached PCR sample tube. In other embodiments, the SCD provided to the testing module may have no PCR sample tube. In those embodiments, the testing module may include mechanisms configured to retrieve a PCR sample tube from a storage rack or other source within the housing and configured to attach the PCR sample tube to the SCD following receipt of the SCD by the testing module. In an alternative embodiment, the PCR sample tube and/or a sample container portion of the containing the biological specimen sample may be separated from the SCD or from the swab, respectively, prior to the sample being deposited in the testing module.

Figure 2:
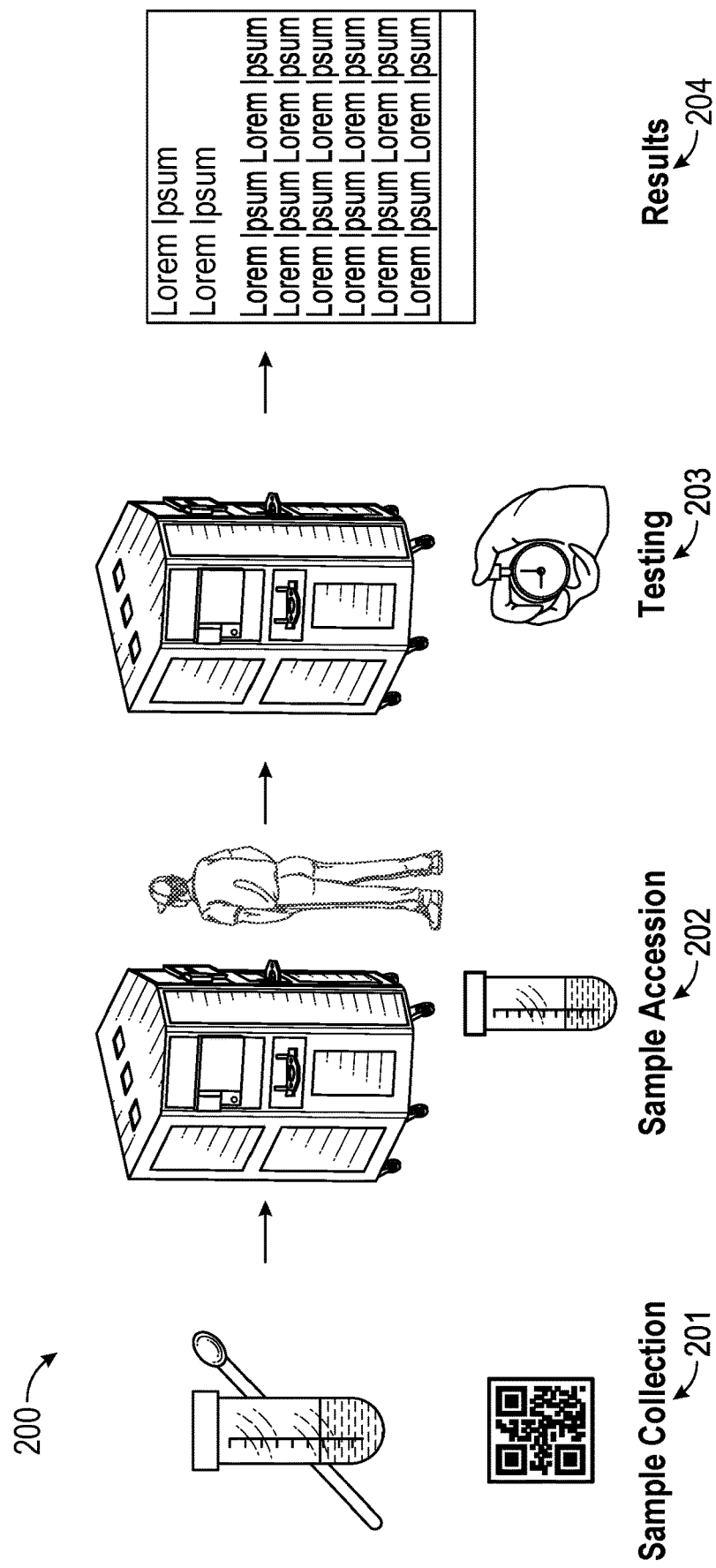
FIG. 2 is an example process flow of a consumer (patient) experience using a localized diagnostics testing system.

The SCDs described herein are single use consumable devices that will facilitate rapid PCR testing at a point of care site or other locations of convenience to patients, office workers, travelers, etc. FIG. 2 depicts an example process flow 200 of the consumer (e.g., user or patient) experience. The process flow 200 may consist of several stages, including the Sample Collection 201, Sample Accession 202, Sample Testing 203, and Results 204 Stages.

During the Sample Collection Stage 201, the SCD is distributed to patients, such as employees, guests, or consumers. Each SCD has an affixed barcode or QR code, to identify the specific SCD and associate it with a particular patient. The SCD is scanned, for example, using a badge or an application. The SCD is used to collect a biological sample from a patient as described herein. The patient may self-collect the sample or another person may assist the patient in collecting the sample. Once the sample is collected, the sample is deposited into the system during the Sample Accession Stage 202. Specifically, the SCD and, therefore, the sample is placed into a machine for processing. The machine is referred to herein as the local testing module. In embodiments, the sample is placed into the testing module by a patient or other user following instructions or by a trained healthcare provider. The testing module is described in more detail in FIGS. 3A-B.

Referring again to FIG. 2, once the sample enters the testing module, the Testing Stage 203 begins. During the Testing Stage 203, the sample is tested using PCR, for example to identify a particular agent in the biological sample. For example, the agent may be RNA indicative of the SARS-CoV-2 virus. The testing module may run at a defined frequency and test up to 192 samples and hour. The Testing Stage 203 may last approximately 30 minutes, after which it reports results. During the Results Stage 204, the results of the Testing Stage 203 are reported to the patient/user. The results may indicate that the patient is positive or negative to a particular illness. In embodiments, the results may be reported on a screen attached to the testing module. In embodiments, the results may be reported to the user via an app, email, and/or text message. The results may also be reported to a third-party (as permitted and consistent with patient privacy regulations) such as appropriate healthcare authorities or the patient's doctor.

FIGS. 3A-3B depict an example PCR testing module 300. FIG. 3A shows an external view of the testing module 300, and FIG. 3B is a partially transparent view to show some of the internal components of the testing module 300.

The testing module 300 may include one or more patient interfaces 302 for the user/patient to use the testing module. The user interface 302 may comprise an interactive screen. The user interface 302 may assist the user in various ways, including but not limited to providing instruction to the user, accepting payment for the test, identification of the user, and/or output of test results, including prior test results. Some or all of these user interface functions may alternatively or additionally be provided to the user via email, text message, app or webpage.

In embodiments, the testing module may include a first scanner configured to read a first machine-readable code on the SCD and a second scanner configured to read a second machine-readable code on the PCR sample tube. Examples of the first and second machine-readable code include barcodes, QR codes, and the like. The first and second codes may be the same as or different from one another. The first scanner may be configured to read a machine-readable code on the SCD received by, or to be received by, the sample input station.

The testing module 300 includes one or more sample input stations 304 for receiving the SCD. The testing module 300 may separate the sample tube and/or sample container containing the sample from the SCD within the device; alternatively, the sample tube and/or sample container containing the sample may be separated from the SCD prior to being deposited in the testing module 300. The testing module 300 includes one or more PCR machines 306, and processing units 308, for handling the SCDs and PCR sample tubes. The testing module 300 also comprises a HEPA filter unit 310 and exhaust ports 312.

The testing module 300 may include a consumables storage area 314 for waste disposal bins 316, for easy collection of waste (e.g., used SCDs). Disposal bay doors 318 allow for access to the consumable storage area 314. The testing module 300 may also include an electrical cabinet 320 which may be accessed through a maintenance access door 322.

In operation, once the SCD is inserted in the testing module 300, the testing module will interact with this SCD, extract the biological specimen sample, lyse it, mix it with water and lyophilized master mix, and present this mixture in the attached PCR sample tube, which in particular embodiments, is a standard 0.2 ml sample tube, as known in the art. The sample container of the SCD and the PCR sample tube will then be separated (as shown in FIG. 1), with the sample tube then being sealed and processed in a PCR machine 306 while the SCD is discarded.

Figure 4:
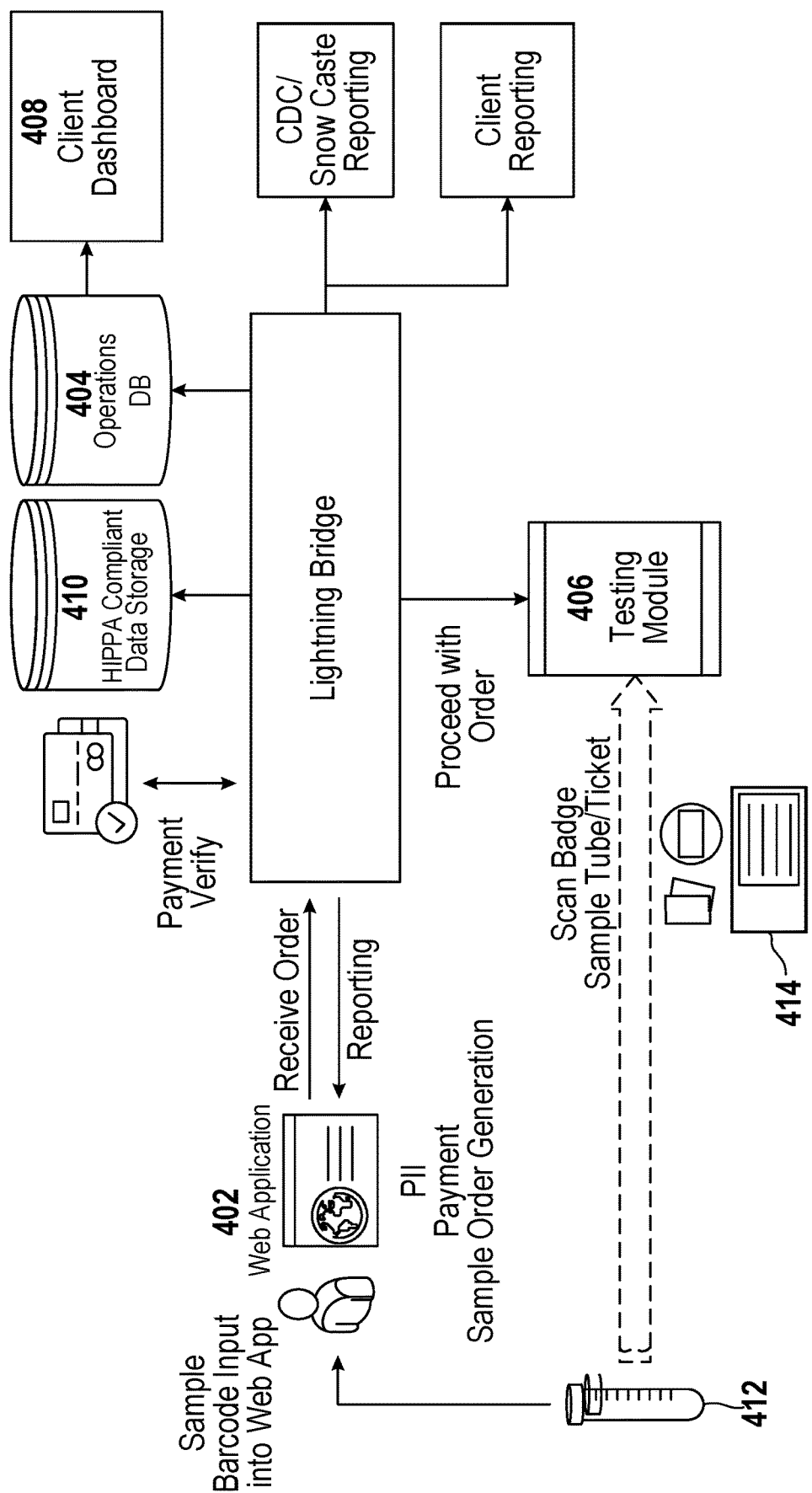
FIG. 4 is an example process flow for managing data in a localized diagnostics testing system as described herein.

FIG. 4 is an example process flow for managing data in the local diagnostics testing system. Embodiments may include a secure tunnel that can be utilized to intake order information from a web application 402, store some of the info into one or more databases 404, 410, and complete the data exchange between various testing modules 406, databases 404, user intake portal, health reporting, result dashboard, and/or system monitoring services. Specifically, a sample's 412 barcode input may be entered via web app 402 or by scan of a badge 414 (e.g., a corporate ID badge) or ticket by the testing module 406. Once the order is received payment may be requested and verified, for example, by communications with a payment processor as known in the art. The results of the PCR test may be stored in a HIPPA compliant database 410, and reported to the client and/or appropriate authorities, such as the Centers for Disease Control (CDC). A client (e.g., an owner or administrator of the testing module) may enter information and/or receive operational information (e.g., testing module status, usage history, consumables inventory within the testing module, etc.) through a client dashboard 408.

Use of the SCDs described herein may include one or more of the following operations: 1) a patient performs identification and financial transaction on the testing module; 2) the testing module dispenses a packaged SCD comprising a unique barcode, QR code, or other identifier associated with the patient in accordance with the identification and financial transaction; 3) the patient opens the package and withdraws the SCD kit; 4) the testing module presents instructions to the patient for use of the SCD kit; 5) the patient inserts an absorbent swab portion of the swab stick part of the SCD kit in their mouth or nose to collect a suitable biological specimen; 6) the patient inserts the swab stick into the sample container; and 7) the patient inserts the combined swab stick and sample container, i.e., the SCD, into the testing module. The testing module processes SCD and then discards it following separation of the PCR sample tube.

In some embodiments, the PCR machine performs a PCR test on the sample to amplify genetic material of interest. It is understood that any method known in the art for amplifying genetic material may be used, including standard PCR, qPCR, RT-PCR, RT-qPCR, and hot start PCR. In embodiments, the testing module may have more than one PCR machine and be able to perform more than one type of PCR. In some embodiments, the PCR machine runs a PCR test of the PCR sample tube contents to determine whether the lysed biological fluid sample includes a particular RNA, such as one indicative of a particular pathogen. For example, the RNA may be one indicative of the SARS-CoV-2 virus. Accordingly, the test module may generate PCR test results that enable diagnosis of one or more particular diseases or illnesses.

One or more illustrative embodiments of the disclosure have been described above. The above-described embodiments are merely illustrative of the scope of this disclosure and are not intended to be limiting in any way. Accordingly, variations, modifications, and equivalents of the embodiments disclosed herein are also within the scope of this disclosure. The above-described embodiments and additional and/or alternative embodiments of the disclosure will be described in detail hereinafter through reference to the accompanying drawings.

Illustrative Embodiments and Use Cases

In some embodiments, the sample collection device may be provided in a two-part kit, which may be sterilized within flexible packaging prior to use. FIG. 1A depicts an example sample collection device (SCD) 100, comprising a first part 102, which includes an absorbent swab 101 mounted on a convenient holder 103, sometimes referred to as a swab stick 102, and a second part 104 which includes a sample container. The absorbent swab 101 may be inserted in the mouth of a patient to absorb saliva pooled in the mouth. Alternatively, the absorbent swab 101 may be inserted into the nasal cavity. After sample collection, the absorbent swab 101 is inserted into the sample container 104, as illustrated in FIG. 1B.

The sample container 104 has features that enable 1) bulk sample extraction from the swab stick 102; 2) lysis of the bulk sample; 3) and PCR sample tube attachment; and 4) metering of a micro sample (~5 µl) of the biological sample from the bulk sample, and transferring the micro sample to the PCR sample tube. The PCR sample tube is pre-sealed prior to attachment to the sample container 104 and may contain a lyophilized master mix as known in the art. For example, a suitable lyophilized master mix for use in PCR detection of pathogens in biological samples may include PCR buffer, cofactor (e.g., $MgCl_2$), dNTPs, probes (e.g., dye), and enzymes (e.g. polymerase and reverse transcriptase). In embodiments, primers, the sample, and water are added to the lyophilized master mix. In embodiments, if the testing module is configured to detect only a specific pathogen, the primers may be lyophilized and included in the master mix.

Figure 1B:
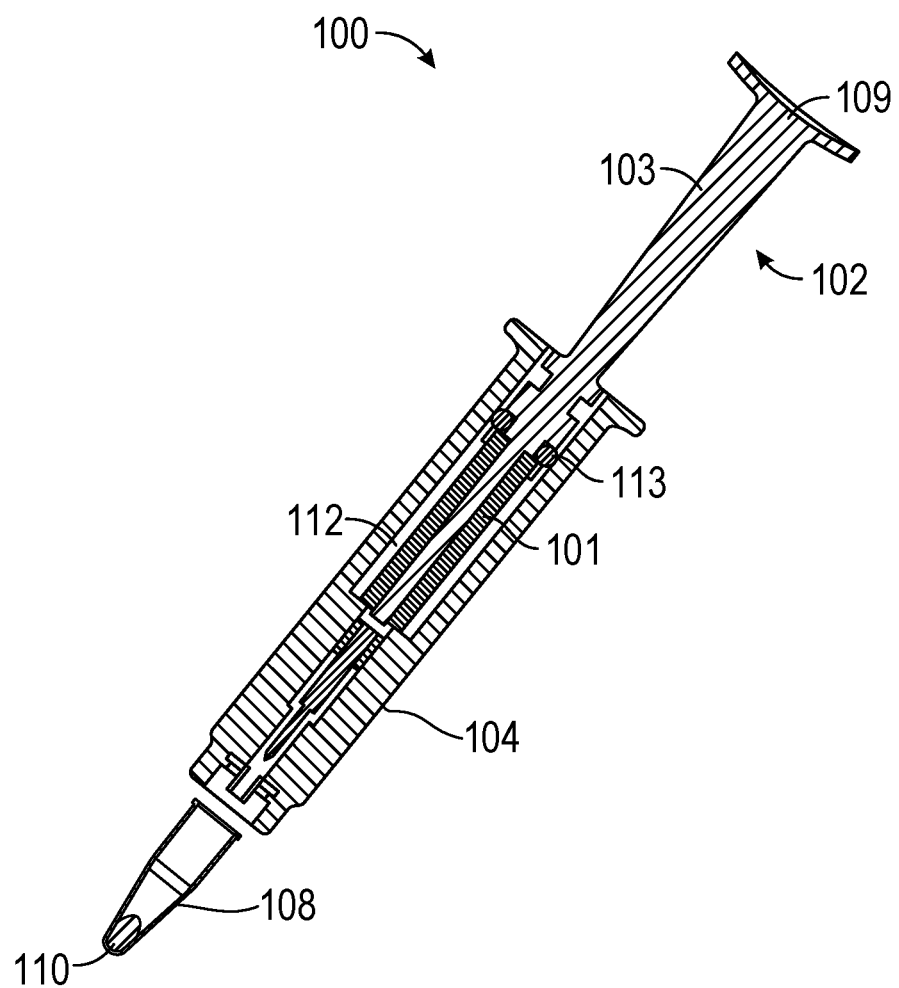
FIG. 1B is a cross-sectional view of an example SCD, according to one embodiment.

FIG. 1B shows an example SCD 100 with a swab stick 102 inserted into sample container 104, which is configured to be attached to PCR sample tube 108, which pre-loaded with a lyophilized master mix 110. In embodiments, the lyophilized master mix 110 may include a suitable chemical lysate known in the art. The swab stick 102 includes a plunger 109 that acts as a handle for the patient to hold during collection of a biological specimen and for guiding the absorbent swab 101 into the sample container 104. The swab stick also includes a sealing member 113, which may be an elastomeric material, for forming a fluid tight seal with an interior surface of a swab receiving chamber 112 in the sample container 104. The sealing member 113 may be disposed between the plunger 109 and the absorbent swab 101, and configured to matingly engage with the interior surface of the swab receiving chamber 112.

Figure 1C:
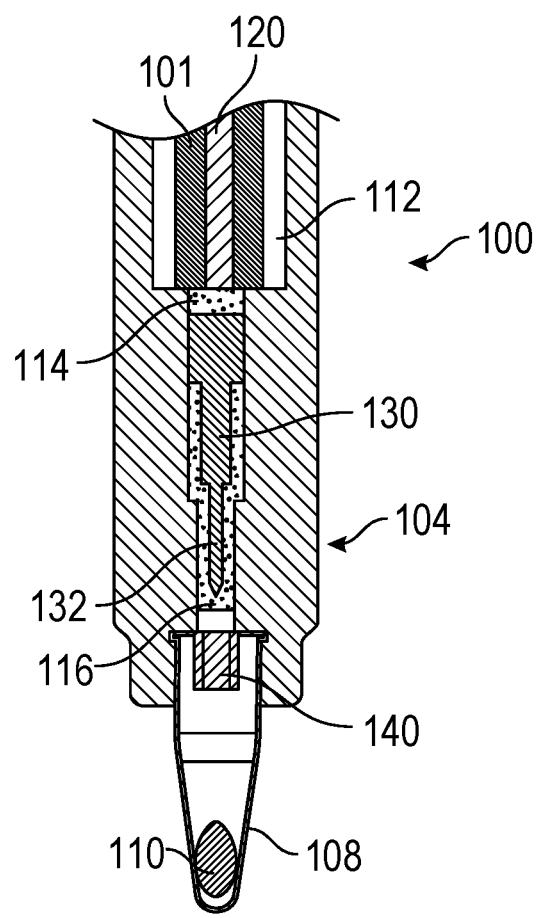
FIG. 1C is close-up, cross-sectional view of a portion of an example SCD with connected sample container, according to one embodiment.

FIG. 1C is a close-up cross-sectional view of part of SCD 100. Sample container 104 is shown with swab chamber 112 having received the saliva swab 101. The swab chamber 112 is in fluid communication with a bulk saliva collection chamber 114, which is configured to receive saliva extracted/transferred from the saliva swab 101. A micro sample chamber 116 is in fluid communication with the bulk saliva collection chamber 114, distal to the swab chamber. The micro sample chamber 116 is dimensioned/configured to hold a selected volume, e.g., about 5 µl, of the saliva transferred from the bulk saliva collection chamber. The sample container 104 includes a metering piston 130 with a piercing tip 132.

The sample container 104, as shown, is releasably attached to a PCR sample tube 108, which contains a lyophilized master mix 110. The attachment may be by frictional engagement. The PCR sample tube attachment may be performed by the testing module after the SCD containing the collected biological specimen has been inserted into the testing module, or the PCR sample tube attachment may be performed by a user before the SCD containing the collected biological specimen is inserted into the testing module. The sample container also includes a projection 140 which is configured to pierce a seal on the top of the PCR sample tube 108 upon the attachment of the PCR sample tube 108 to the sample container 104. The projection 140 includes a through-channel that is in communication with the micro sample chamber 116.

After initial insertion of the saliva swap into the sample container, the saliva swab may be translated into the swab chamber 112 a first distance that will compress the saliva swab 101 and thereby release collected saliva into the bulk saliva collection chamber 114. After chemical or thermal lysing of the saliva in the bulk saliva collection chamber 114, further downward translation of the saliva swab into the swab chamber 112 a second distance will drive swab plunger 120, which extends from the holder 103, into contact with the metering piston 130 and drive at least part of the metering piston into the micro sample chamber 116, and displace the selected volume of the lysed saliva from the micro sample chamber 116 into the PCR sample tube 108. These translations of the first and second distances are performed in and by the testing module.

Figure 1D:
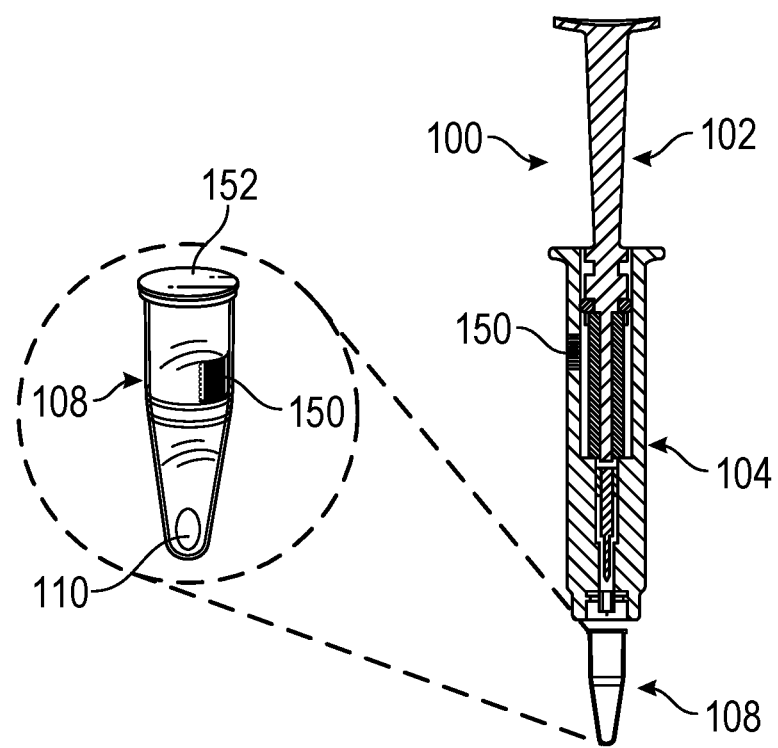
FIG. 1D depicts an example CD and PCR sample tube, which each have a barcode for sample tracking, according to one embodiment.

As shown in FIG. 1D, each SCD 100, and each PCR sample tube 108 includes a unique barcode, QR code, or the like 150. This is used to allow the testing module to properly track/associate a patient's sample with the ultimate results from the PCR test. As shown, the PCR sample tube 108 includes a seal 152, which may be a thin foil or polymeric film, and a master mix 110 contained within the interior space defined by the sample tube walls.

In one embodiment, SCD 100 is processed by a testing module after a patient uses the swab stick to collect a sample, places the swab stick in the sample container, and then deposits the swab stick and the sample container into the testing module. The testing module then may load a sample tube, e.g., from a storage rack, and dispense a predetermined quantity of water (e.g., ~15 uL) into the sample tube. The water may rehydrate the lyophilized master mix in the sample tube. The testing module then may attach the sample tube to the SCD as described above. The testing module then may depress the swab plunger to compress the absorbent swab so that saliva is released into the bulk saliva collection chamber. The testing module may stop pressing the plunger after translating a programmed distance. The testing module then may apply thermal energy to the sample container effectively to heat the bulk saliva to 95° C. for several minutes and lyse the saliva sample. The testing module then may continue to depress the plunger, which in return causes the metering piston (i.e., piercing plunger) to translate into the micro sample chamber to eject 5 µl of the lysed saliva sample into the attached PCR sample tube. The testing module then applies ultrasonic energy to mix together the components in the PCR sample tube. Then, the testing module separates the SCD from the PCR sample tube and then seals the sample tube, e.g., with a film or foil material known in the art. The testing module then may place the PCR sample tube in a PCR machine and run a PCR test on the same in the PCR sample tube. The testing module may discard the used SCD into a waste receptacle. Once the PCR test is complete, then the testing module may also discard the sample tube into a waste receptacle.

Figure 5B:
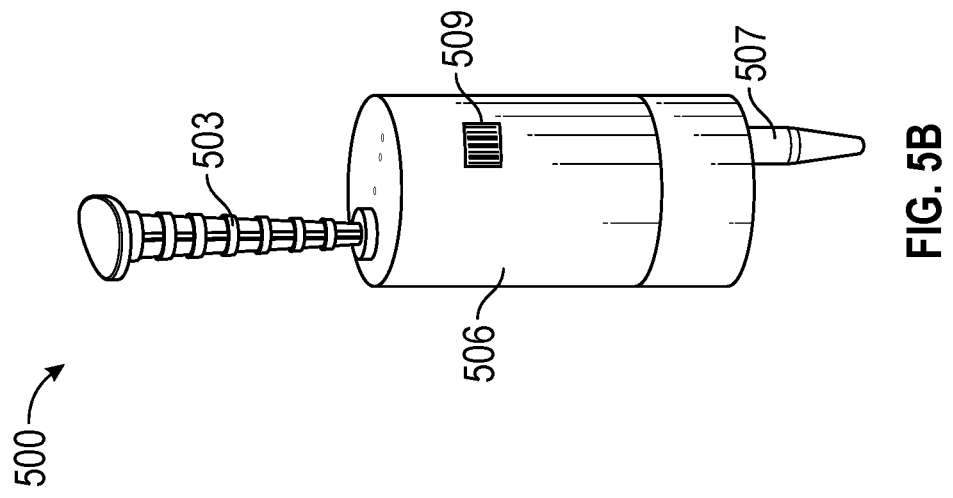
FIGS. 5A-5B are perspective views of an example SCD, according to one embodiment of the present disclosure.
Figure 5A:
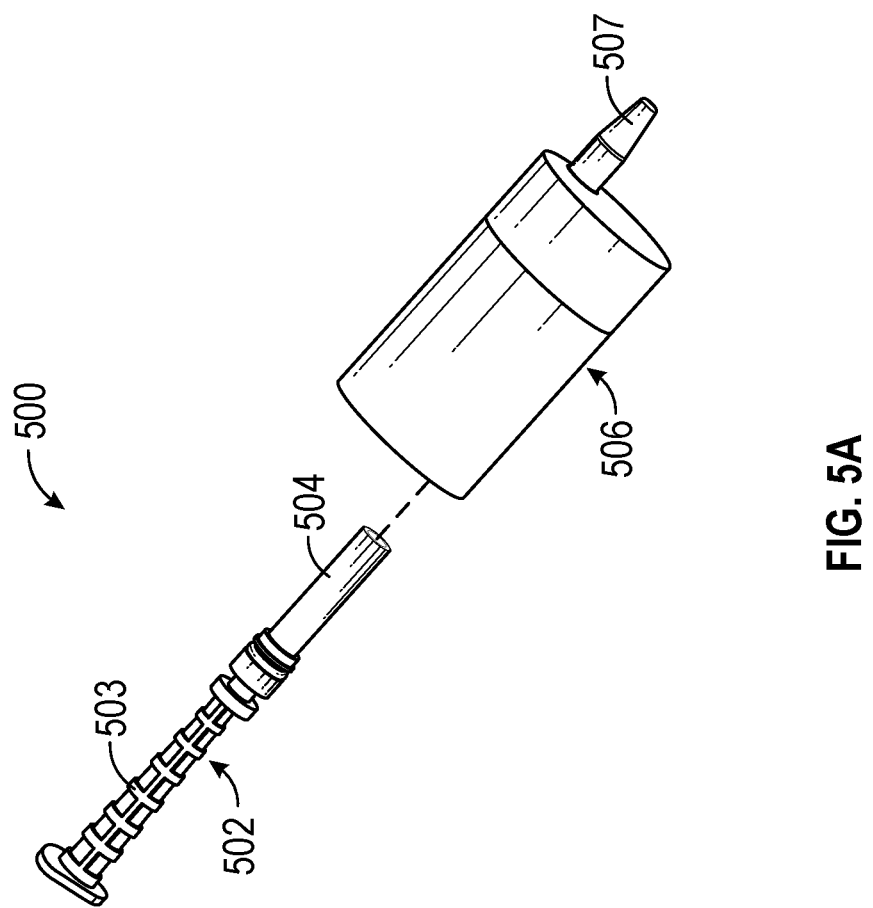

Another embodiment of a sample collection device 500 is illustrated in FIGS. 5A-5F. The SCD 500 includes a swab stick 502, a sample container 506, and PCR sample tube 507. The swab stick 502 comprises a plunger handle 503 and an absorbent swab 504. The absorbent swab may be a saliva swab. The sample container 506 includes a barcode, QR code, or the like 509. In embodiments, the entire SCD 500 as depicted in FIG. 5B is inserted into the testing module.

As shown in FIGS. 5C-5F, the sample container 506 includes swab chamber 512 for receiving the absorbent swab 504. The top of the sample container 506 includes an opening to access the swab chamber 512, as well as a separate air vent 580 opening and openings to receive a water chamber piston 510 and a metering piston 508. The swab chamber 512 is in fluid communication with a bulk saliva collection chamber 514, which is configured to receive saliva 600 extracted/transferred from the absorbent swab 504. A micro sample chamber 516 is in fluid communication with the bulk saliva collection chamber 514. The micro sample chamber 516 is dimensioned/configured to hold a selected volume, e.g., about 5 μl, of the saliva from the bulk saliva collection chamber. The selected volume may be referred to as a "microportion", which may be from 1 μl to 10 μl, for example.

The sample container 506 includes a water chamber 575, which may be loaded with a predetermined quantity of water, for receiving the water chamber piston 510. The water chamber piston 510, which may have a piercing tip configured to pierce a seal on the sealed PCR sample tube, is dimensioned to be inserted through the water chamber 575 and extend at least partially through the seal on the PCR sample tube to create an opening in the seal to permit water from the water chamber 575 to enter the PCR sample tube 507 to contact/rehydrate a dried/lyophilized master mix 517 contained therein.

The sample container 506 also includes a saliva piston metering channel 560 for receiving the metering piston 508. The saliva piston metering channel 560 is in fluid communication with the micro sample chamber 516 and also may be in fluid communication with the bulk saliva collection chamber 514. The metering piston 508 may have a piercing tip configured to pierce a seal on the sealed PCR sample tube 507. The metering piston 508 is dimensioned to be inserted through the saliva piston metering channel 560 and extended at least partially through the seal on the PCR sample tube to create an opening in the seal to permit the selected volume of the saliva from the micro sample chamber 516 to enter the PCR sample tube 507.

Figure 5F:
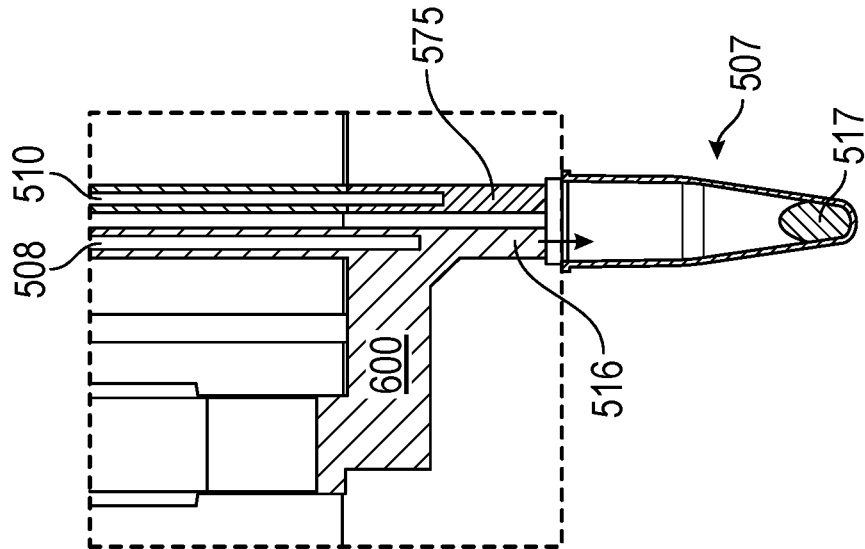
FIGS. 5E-5F are close-up cross-sectional views of a portion of an example SCD, illustrating operations therein when the plunger is pressed, according to one embodiment of the present disclosure.
Figure 5E:
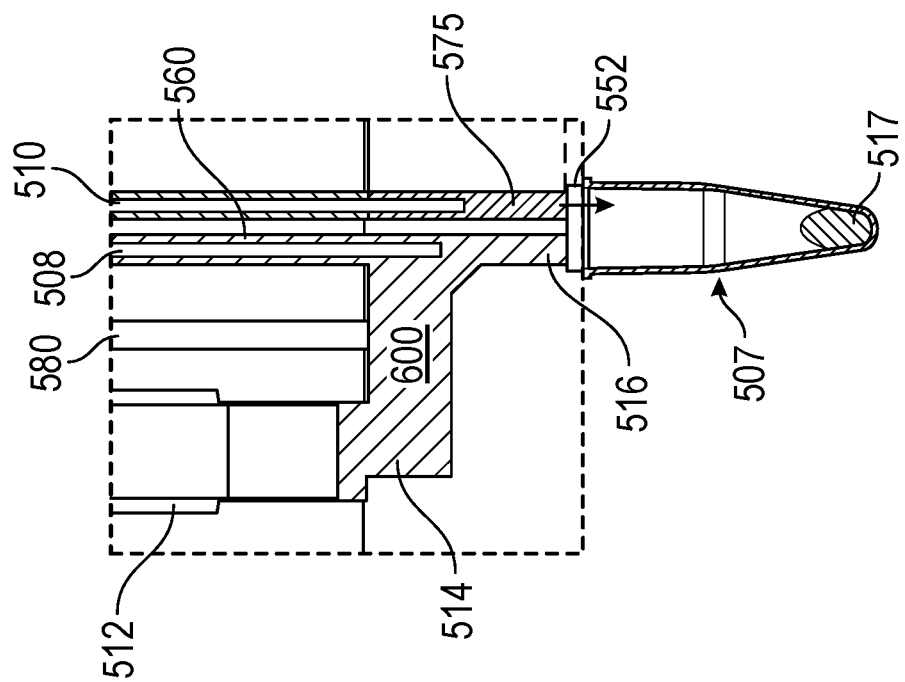

In use, fluid flow within the sample container 506 may be more clearly understood with reference to FIGS. 5E-5F. After collection of a saliva specimen, the absorbent swab 504, containing the saliva specimen, is inserted into swab chamber 512. Then, the SCD 500 is inserted into a testing module, which may carry out the following operations. The absorbent swab 504 is compressed to release the saliva specimen 600 (similarly to operation of the swab and sample container in SCD 100 described above) into the bulk saliva collection chamber 514. Simultaneously, air displaced by the saliva entering the bulk saliva collection chamber 514 may escape through the air vent 580 to equalize the pressure within the bulk saliva collection chamber 514.

Subsequently, the saliva in the bulk saliva collection chamber 514 is lysed. In an embodiment, the saliva is thermally lysed. In some embodiments, the saliva or other sample may be lysed using chemical reagents known in the art. In some embodiments, the chemical lysing agents may be pre-loaded in the SCD. The lysing may include a combination of chemical and thermal lysing.

Saliva is permitted to flow from the bulk saliva collection chamber 514 into the micro sample chamber 516. This may occur before or after lysing, depending on the position of the metering piston 508, which may control flow of the saliva from the bulk saliva collection chamber 514 into the micro sample chamber 516, as well as into the PCR sample tube 507. Specifically, when the metering piston 508 is inserted into the micro sample chamber 516, it may block flow of saliva from flowing from the bulk saliva collection chamber 514 into the micro sample chamber 516. When the metering piston 508 is in a retracted configuration, such as illustrated in FIGS. 5E-5F, or removed from the saliva piston metering channel 560, such as illustrated in FIG. 5D, then saliva is able to flow from the bulk saliva collection chamber 514 into the micro sample chamber 516.

At the appropriate time for rehydration of the master mix 517 in PCR sample tube 507, the water chamber piston 510 is inserted through the water chamber 575 and pierces the seal 552, covering the PCR sample tube 507, causing water located in the water chamber 575 to enter the PCR sample tube 507, as indicated by the arrow in FIG. 5F, to contact/rehydrate the master mix 517 contained therein.

Before, contemporaneously, or after the water is added to the PCR sample tube 507, the metering piston 508 is inserted through the saliva piston metering channel 560 and pierces the seal 552 on the PCR sample tube, causing the selected volume, e.g., 5 μl, of the lysed saliva to flow from the micro sample chamber 516 into the PCR sample tube 507, as indicated by the arrow in FIG. 5E.

Once the PCR sample tube 507 contains the water, master mix 517, and the selected volume of the lysed saliva, the testing module then applies ultrasonic energy to mix together the components in the PCR sample tube. The testing module then separates the SCD from the PCR sample tube and then seals the sample tube, e.g., with a film or foil material known in the art. The testing module then may place the PCR sample tube in a PCR machine and run a PCR test on the same in the PCR sample tube. The testing module may discard the used SCD into a waste receptacle. Once the PCR test is complete, then the testing module may also discard the sample tube into a waste receptacle.

FIGS. 6A-6B depict an example nasal sample collector 1500. The nasal sample collector 1500 may include a moistened open-cell foam 1502, a holding cap 1504, and a tip (nasal swab) 1506 comprising an adsorbent material. In embodiments, the sample collector 1500 is packaged in a provided water-impermeable packaging to prevent water in the moistened foam from evaporating. Once the packaging is opened, the nasal swab tip 1506 would be inserted into the anterior nares of a patient. The sample collector 1500 is then inserted into a sample holder 1508. Application of force to the holding cap 1504 squeezes the foam 1502, expelling the water/liquid in the foam 1502 to flow over the nasal swab 1506 and carrying the collected nasal sample into a collection tube (not shown) for further processing as described herein. The collection tube may be adapted to include features of the saliva sample container described herein.

Figure 7B:
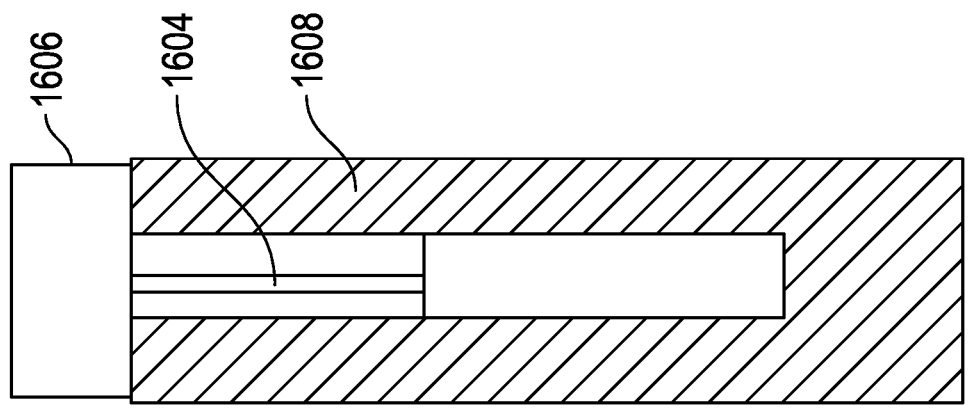
FIGS. 7A-7B depict an example nasal SCD, according to one embodiment of the present disclosure.
Figure 7A:
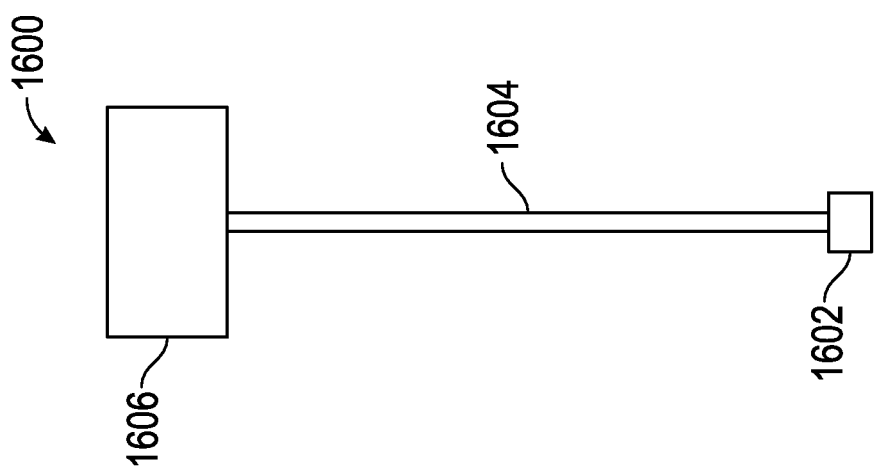

FIGS. 7A-7B, show an example nasal sample collection device 1600. The sample collection device 1600 includes a first part that includes a nasal swab 1602 attached to a cap 1606 by a rod 1604 extending from the cap, and a second part that includes a collection tube 1608 which is in a dry state, i.e., it initially contains no liquid. In an initial configuration (FIG. 7A), the cap 1606 contains therein a liquid solvent (e.g., water). After a nasal sample is collected from the patient's nose by the nasal swab 1602, the cap 1606 is secured onto the collection tube 1608 to release the liquid solvent from the cap 1606 into the collection tube 1608, for example, by a twist release mechanism.

Figure 8B:
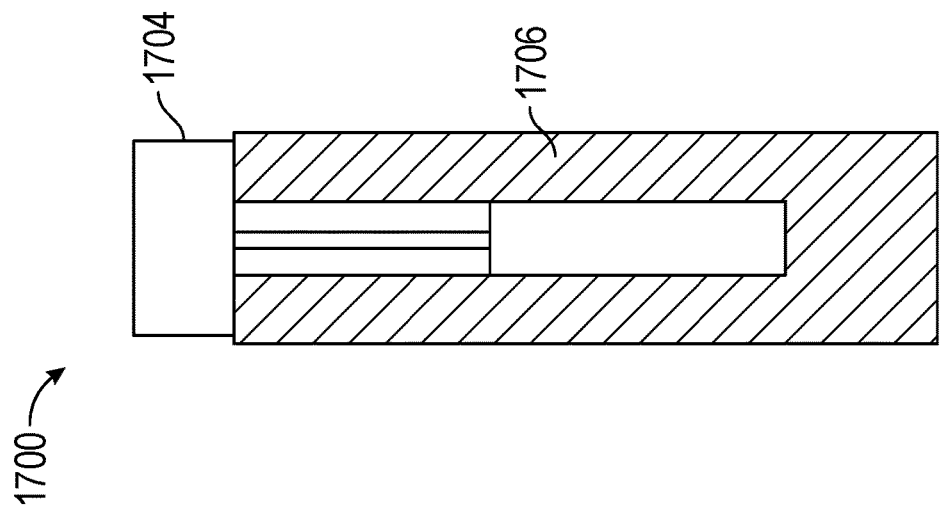
FIGS. 8A-8B depict an example nasal SCD, according to one embodiment of the present disclosure.
Figure 8A:
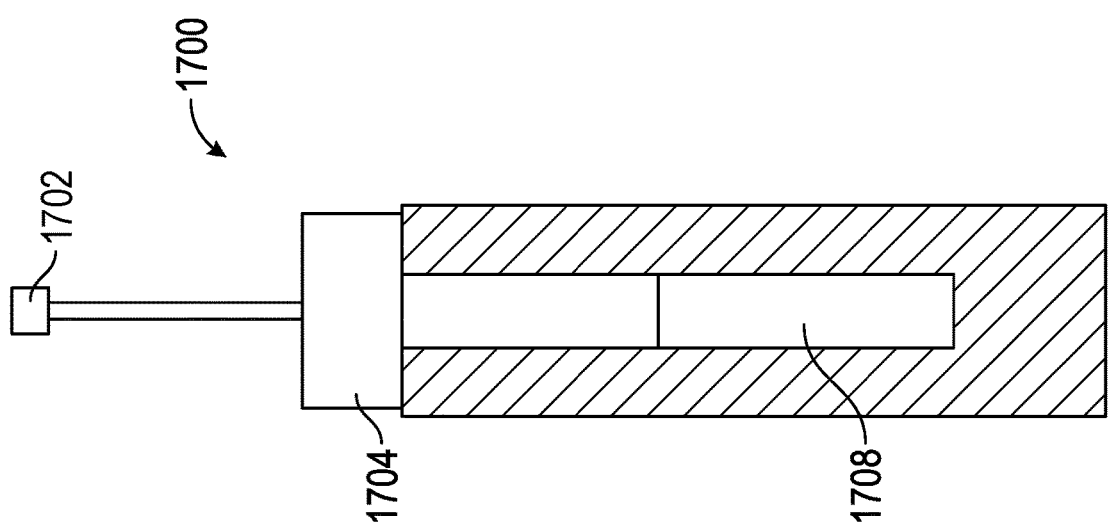

FIGS. 8A-8B illustrate an example nasal sample collection device 1700, which includes a collection tube 1706 which contains a liquid solvent (e.g., water) 1708 and a cap 1704. In an initial configuration (FIG. 8A), the cap 1704 is secured onto the collection tube 1706, sealing the liquid solvent therein, with the swab 1702 extending outside of the collection tube 1706. For use, a patient may detach the cap 1704 from the collection tube, collect a nasal sample from the patient's nose, insert the swab 1702 into the collection tube 1706; and re-secure the cap 1704 (in the opposite orientation) onto the collection tube 1706 in second, sample-collected configuration (FIG. 8B). The cap and collection tube may include any suitable securement features. For example, the cap may be a reversible threaded closure.

Figure 9:
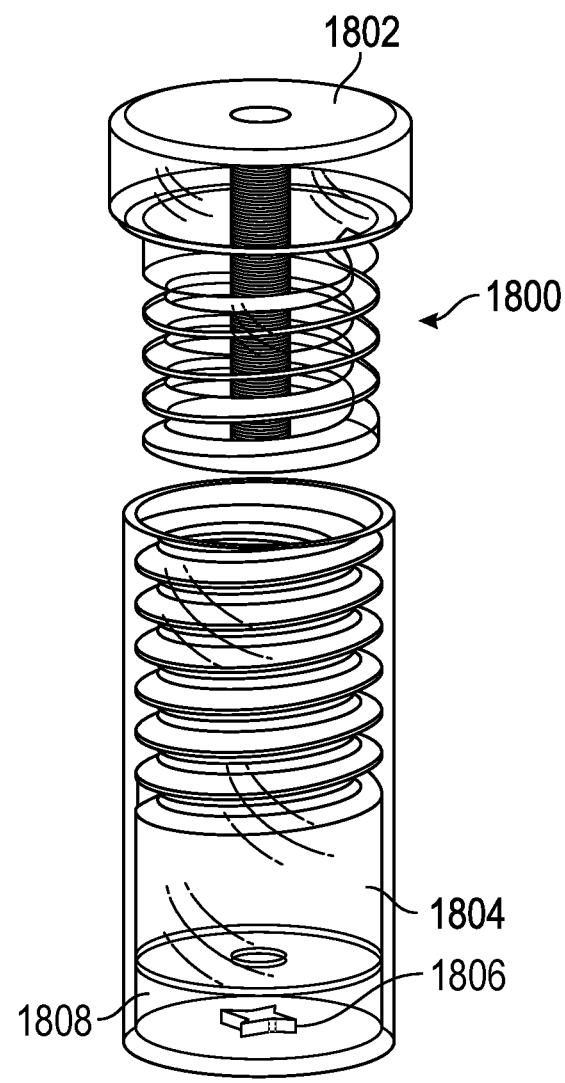
FIG. 9 is an example nasal sample collection tube, according to one embodiment of the present disclosure.

FIG. 9 shows an example nasal sample collection device 1800 which includes a cap 1802 and a sample container 1804. The sample container 1804 includes a bottom chamber 1808 in which lyophilized master mix or other reagent 1806 is contained. The cap 1802 and sample container 1804 are configured to be attached together with a screwing mechanism (mating helical threads and grooves), which may be used to control the distance at which a nasal swab extending from the cap 1802 may be inserted into sample container 1804. After a user collects a nasal sample, the user inserts the swab (not shown) through a hole in the top of the cap 1802. Grooves on the swab and tube cap may prevent liquid from leaking from the sample container 1804. The screw mechanism limits the depth of the swab inside the sample container 1804. The user may screw the cap partially into the sample container, and then after the sample collection device is inserted into a testing module, the testing module can rotate the cap further to push the swab through an opening and into the bottom chamber to facilitate contact and mixing with the reagent in the bottom chamber for subsequent processing in the PCR machine.

Figure 10:
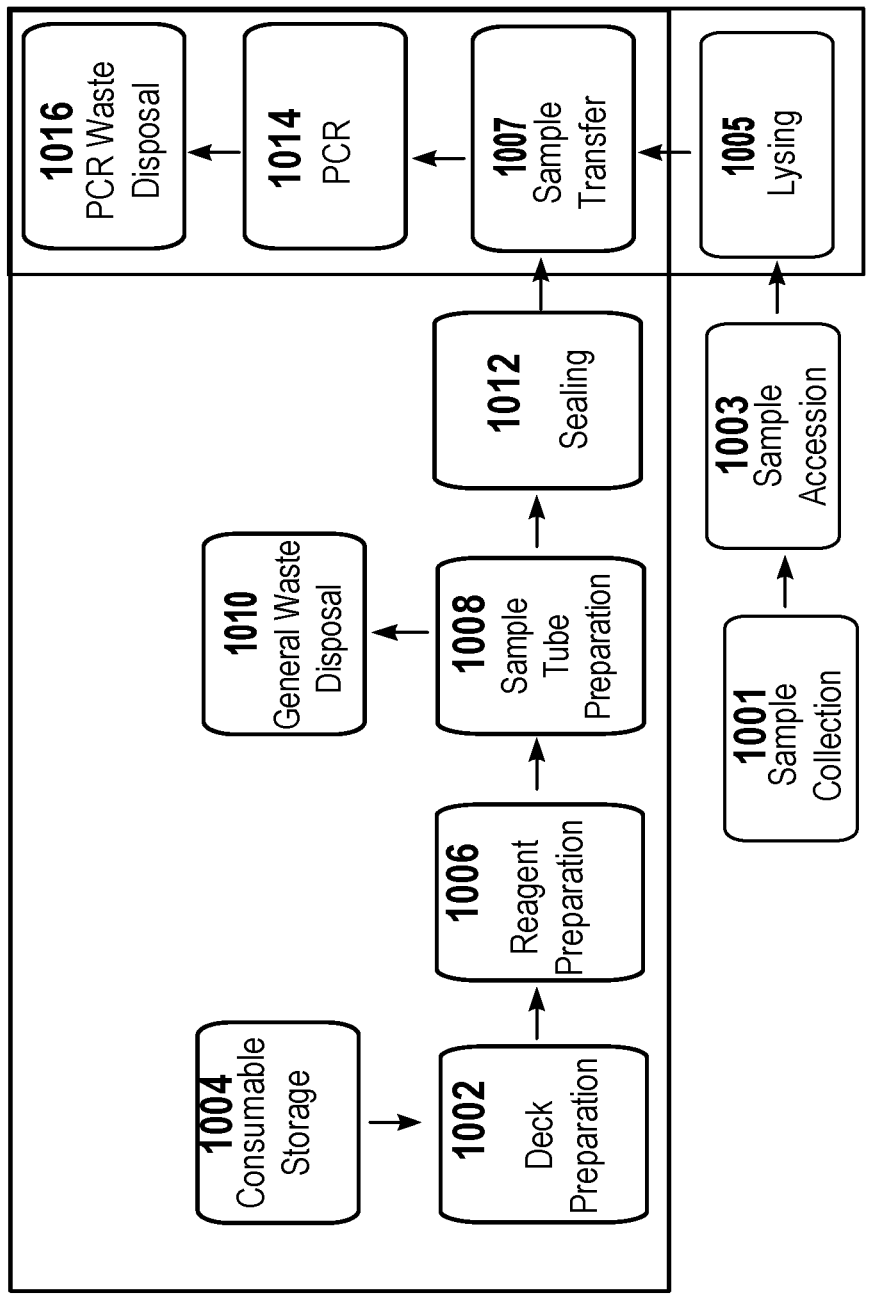
FIG. 10 is an example process flow diagram for rapid PCR testing, according to one embodiment of the present disclosure.

FIG. 10 is an example process flow for rapid PCR testing within a testing module, useful with the presently disclosed SCDs. The testing module may include various components for processing the collected sample within the SCD and within the PCR sample tube. The testing module may include a barcode scanner, one or more robot arms with actuators, reagents, storage for reagents and consumables, reagent plates, water, dispensers, pipette heads, PCR plates, waste receptacles, a plate sealer, and one or more PCR machines. Lysing and inactivation of the sample may be performed by the testing module or separately before the SCD and sample are placed into the testing module. The testing module may scan the sample, prepare reagents and mix them with the sample, prepare and seal a PCR plate, and run it through a PCR machine. The testing module also collects and disposes of the waste used in each step.

As shown in FIG. 10, the testing module may perform various steps to prepare for receipt of the sample. Examples of these steps include deck preparation step 1002, consumable storage step 1004, reagent preparation step 1006, PCR sample tube preparation step 1008, general waste disposal step 1010, and sealing step 1012. Once the sample is received by the testing module, the testing module performs lysing step 1005, sample transfer step 1007, in which the sample is transferred into the sample tube, PCR testing step 1014, and PCR waste disposal step 1016. To prepare for receipt of the sample, the testing module first prepares the deck within the testing module at deck preparation step 1002. The testing module may prepare the deck with the assistance of a robot arm with an actuator. At consumable storage step 1004, the testing module may remove consumables, including reagents, from a storage rack. The testing module may then prepare the reagents at reagent preparation step 1006. Reagent preparation step 1006 may include the use of a reagent plate, dispenser, pipette, and pipette heads. For example, the testing module may mix various reagents together, such as water, polymerase, primers, and/or buffer. At PCR sample tube preparation step 1008, the PCR sample tube is prepared. If a PCR plate is used, then a standard-sized plate, for example, a 6, 8, 12, 24, 48, or 96-well plate, may be used. The testing module optionally disposes of waste at general waste disposal step 1010. Waste disposed at general waste disposal step 1010 may include used pipette tips and reagent plates or PCR sample tubes and used SCDs. At sealing step 1012, the PCR sample tube is sealed, for example, using a film or closure (e.g., cap or plug).

The sample is collected by the user using an SCD at sample collection step 1001. At sample accession step 1003, the sample is subjected to an accessioning process. In FIG. 10, sample accessioning takes place outside the testing module; however, in embodiments, sample accessioning may be performed by the testing module instead. Sample accession step 1003 may include scanning the SCD and/or the PCR sample tube, associating the sample with a specific patient/user, and/or a quality control check of the sample. The sample is then placed in the testing module. At lysing step 1005, the testing module lyses the sample in the SCD. The testing module may also inactivate the sample during lysing step 1005. At PCR step 1014, the testing module adds the lysed sample to the prepared PCR sample tube and performs a PCR test on the sample. At PCR waste disposal step 1016, the testing module optionally disposes of any PCR waste, such as the used PCR sample tube and tested biological sample.

Figure 11:
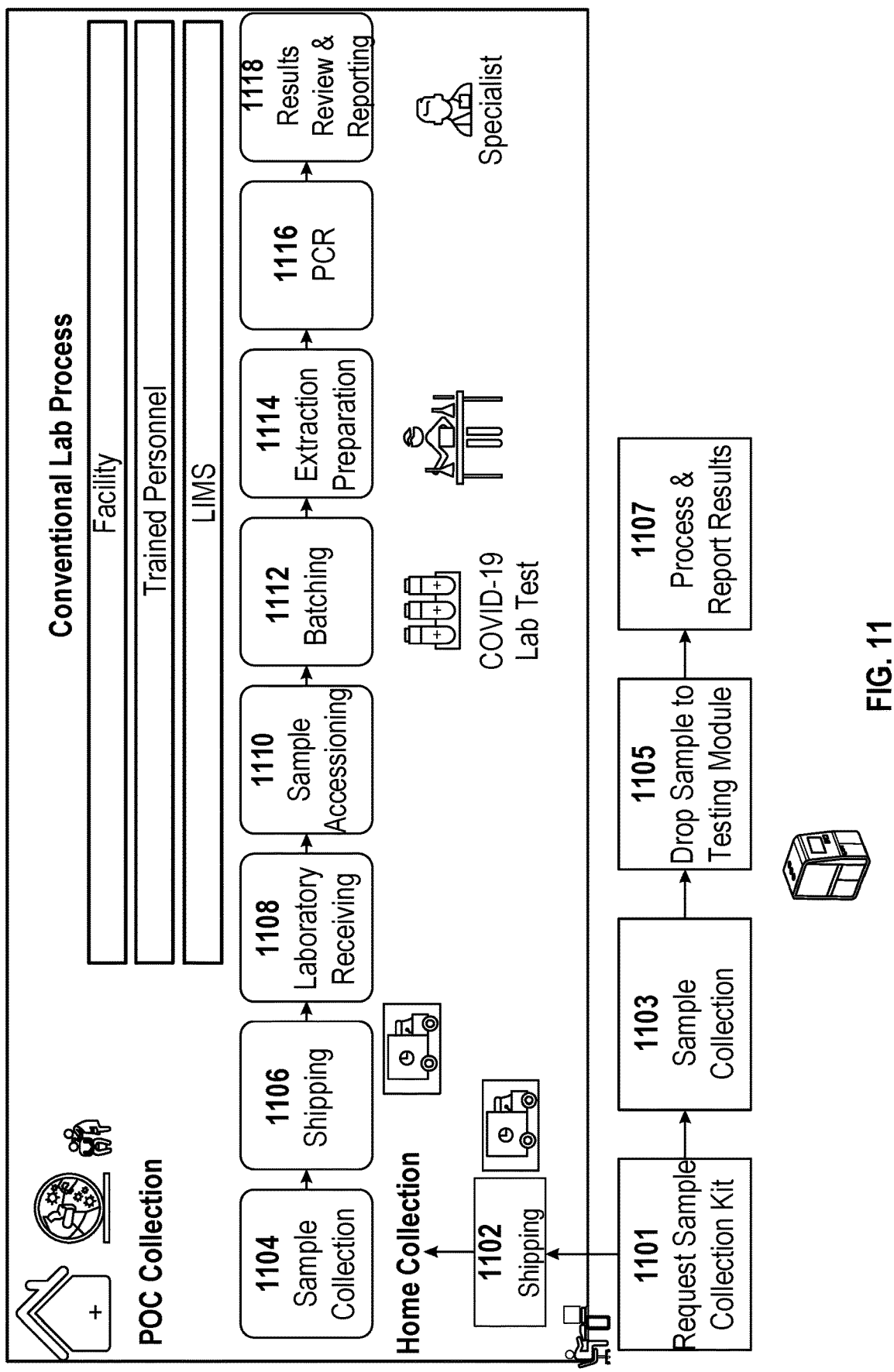
FIG. 11 depicts an example process flow of a conventional lab process of PCR testing contrasted with a rapid method of PCR testing, according to one embodiment of the present disclosure.

FIG. 11 illustrates the time-consuming steps involved in conventional lab processes of PCR testing as compared to the fewer and more rapid steps possible with the method of PCR testing described herein. The conventional lab process may include either a home collection process or a point-of-care collection process done at a mobile or brick-and-mortar health care facility. For home collection, a user must first request a sample collection kit at Step 1101. The sample collection kit is then shipped to the user at Step 1102. The user collects the sample using the shipped sample collection kit at Step 1104. Alternatively, if point-of-care collection is being used, then either the user or a healthcare professional may collect the sample at the point-of-care site at Step 1104. The collected sample is then shipped to a laboratory at Step 1106. At Step 1108, the laboratory receives the sample. At Step 1110, the sample undergoes a sample accessioning process. The sample accessioning process may include labeling, sorting, receipt, and recordation of data about the sample and/or a quality control check of the sample. At step 1112, the sample is batched with other samples. At Step 1114, the sample is prepared for extraction. At Step 1116, a PCR test is performed on the sample, and results are generated. At Step 1118, a specialist reviews the results of the PCR test and reports those results. Conversely, the method of PCR testing described herein includes fewer steps and is faster when compared with conventional lab processes of PCR testing. Using the methods described herein, the user first obtains a sample collection kit at Step 1101. This may occur at the location where the testing module is located (e.g., a pharmacy, a mobile or brick-and-mortar health care facility, an office building, a public transportation center, such as an airport or train station, etc.). At Step 1103, the user uses the sample collection kit (i.e., an SCD) to collect the sample, and then the sample is placed into the testing module at Step 1105, for example, directly by the user or indirectly by another, for example, a healthcare professional. At Step 1107, the testing module processes the sample and reports the results to the user.

Figure 12:
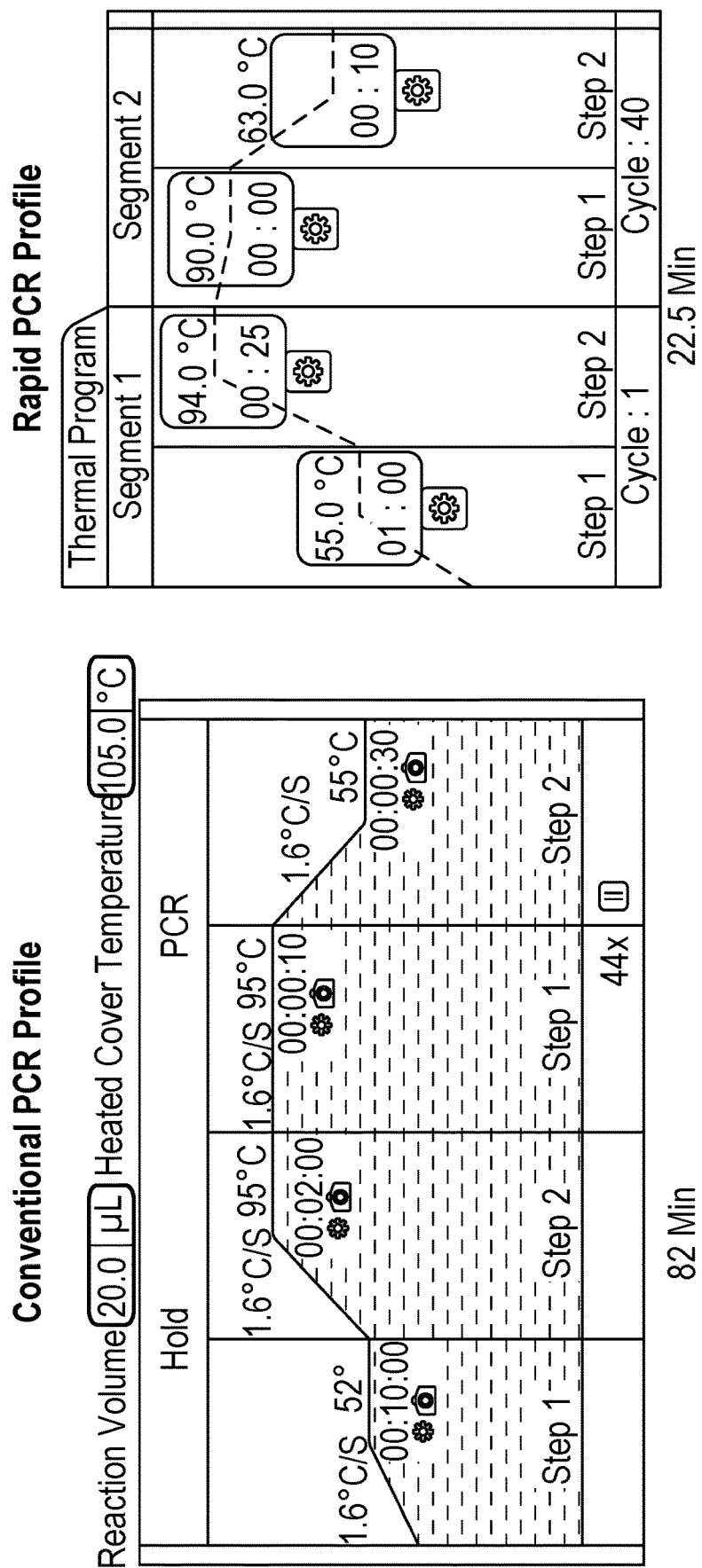
FIG. 12 shows two graphs that illustrate a conventional PCR profile (on left) and a PCR profile according to one example of a PCR profile with the methods and devices described herein (on right).

The presently disclosed SCDs and the local testing modules advantageously may eliminate the need for shipping samples, and may yield a faster PCR profile as compared with PCR profiles provided with conventional testing methods. As shown in FIG. 12, both conventional PCR machines and the testing module perform one or more thermal cycles during PCR testing. Such thermal cycles include raising and lowering the temperature of the sample to assist with the annealing and amplification process, as known in the art. In the illustrated conventional process, the process includes increasing the sample temperature from ambient to 52° C. at 1.6° C./sec, holding for 10 minutes, increasing to 95° C. at 1.6° C./sec, holding at 95° C., and cooling to 55° C. at 1.6° C./sec, with 44 cycles, taking a total of 82 minutes to produce the results. However, the process using the testing module described herein, in the illustrated embodiment, may include increasing the sample temperature from ambient to 55° C., holding, increasing to 94° C., holding, decreasing to 90° C., and cooling to 63° C., with 40 cycles, taking a total of less than 23 minutes to produce the results. In some embodiments, the rates of heating and cooling of the samples in the PCR machine of the testing modules described herein may range from 0.5° C./second to 5.0° C./second. Table 1 below shows various methods of current methods of COVID-19 testing, which are slower and/or provide low throughput.

TABLE 1

| Test Assay | Average TAT | Test W/EUA | Throughput |
|---|---|---|---|
| RT-PCR | >60 minutes | BGI Covid-19, TaqPath COVID-19 combo kit | High throughput |
| RT-PCR (Cartridge or Self Contained Reagent) | ~45 minutes | BioFire Covid-19 test, Xpert Xpress SARS-CoV-2 test | 1 sample per run |
| RT-Lamp (Isothermal) | 30-45 minutes | ID NOW COVID-19, iAMP COVID-19 detection kit | 1 sample per run |
| Micro-Fluidics RT-PCR | 20-40 minutes | VITAPCR SARS-CoV-2 assay | 1 sample per run |
| RT-PCT + Lateral Flow | ~30 minutes | Accula SARS-CoV-2 test | 1 sample per run |

While the devices and methods herein are particularly useful in analyzing clinical specimens for the presence of infectious agents, such as those associated with various viruses, including the SARS-CoV-2 virus and influenza, the sample collection devices and methods described herein also can be used or readily adapted for use in the screening or diagnosis of a variety of other diseases and conditions in which PCR testing may be utilized. Non-limiting examples include measles, mumps, chlamydia, Bordetella pertussis Toxin, tuberculosis, H. Pylori, Zika, mycoplasma pneumoniae, Varicella-zoster virus, VAV, borrelia, Chagas, and sepsis. In other examples, the methods and devices described herein may be used in the screening of various other medical conditions, such as those related to bone and mineral health, thyroid, reproductive endocrinology, anemia, autoimmunity, tumor markers, hypertension, adrenal function, growth, diabetes, viral hepatitis and retroviruses, treponema, Epstein-Barr Virus, TORCH (toxoplasmosis, rubella cytomegalovirus, herpes simplex, and HIV), as well as in stool diagnostics. PCR assays are known in the art for use in the diagnosis of a wide variety of diseases.

Figure 13:
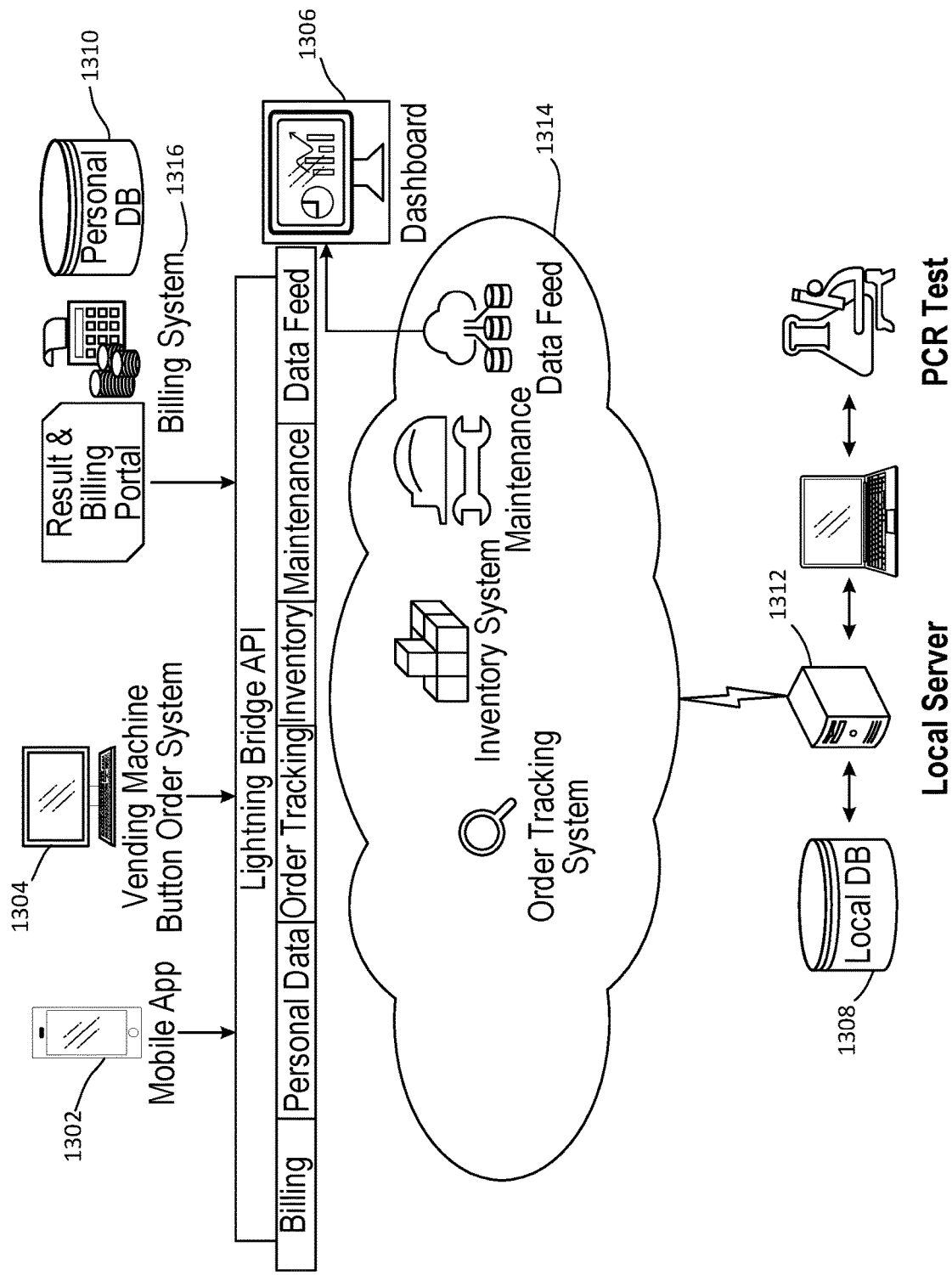
FIG. 13 is an example process flow of software systems supporting the diagnostic sample collection system.

FIG. 13 illustrates one example of information flow in a software system supporting the rapid PCR testing system described herein. For example, the system will enable a patient to order a test online using a mobile device 1302 (or any other suitable computing device, such as a tablet or computer) or (while present at) a local PCR testing module 1312. Computing devices may be in operable communication with the testing module 1312. For example, a phone, tablet, or other mobile device 1302 may be configured to communicate with a controller to provide instructions and/or receive feedback from the software system via one or more networks. The testing module 1312 may be configured to operate like a "vending machine" with buttons (e.g., a keypad) for a user to interface with the testing module 1312, as a vending machine button order system 1304. The system may include a billing system 1316 with a result and billing portal. A B2B dashboard 1306 may be provided to enable effective management of the test module 1312 and related systems, providing maintenance indicators, as well as inventory and replenishment indicators that are user configurable. The testing module software manages end-to-end sample handling and result generation. Data may be stored in a local database 1308 and/or a personal database 1310; however, the testing module 1312 itself is not in possession of patient data. All direct interaction is serviced from the cloud 1314. The cloud 1314 may include an order tracking system, an inventory system, a maintenance system, and a data feed system. The local database 1308 and personal database 1310 may comprise memory for storing data, such as test results and/or computer-executable instructions. When running in offline mode, the testing module 1312 only handles and reports sample barcode results. In embodiments, PCR test results may be sent to a dashboard 1306 and/or mobile device 1302.

Illustrative Computer Architecture

Figure 14:
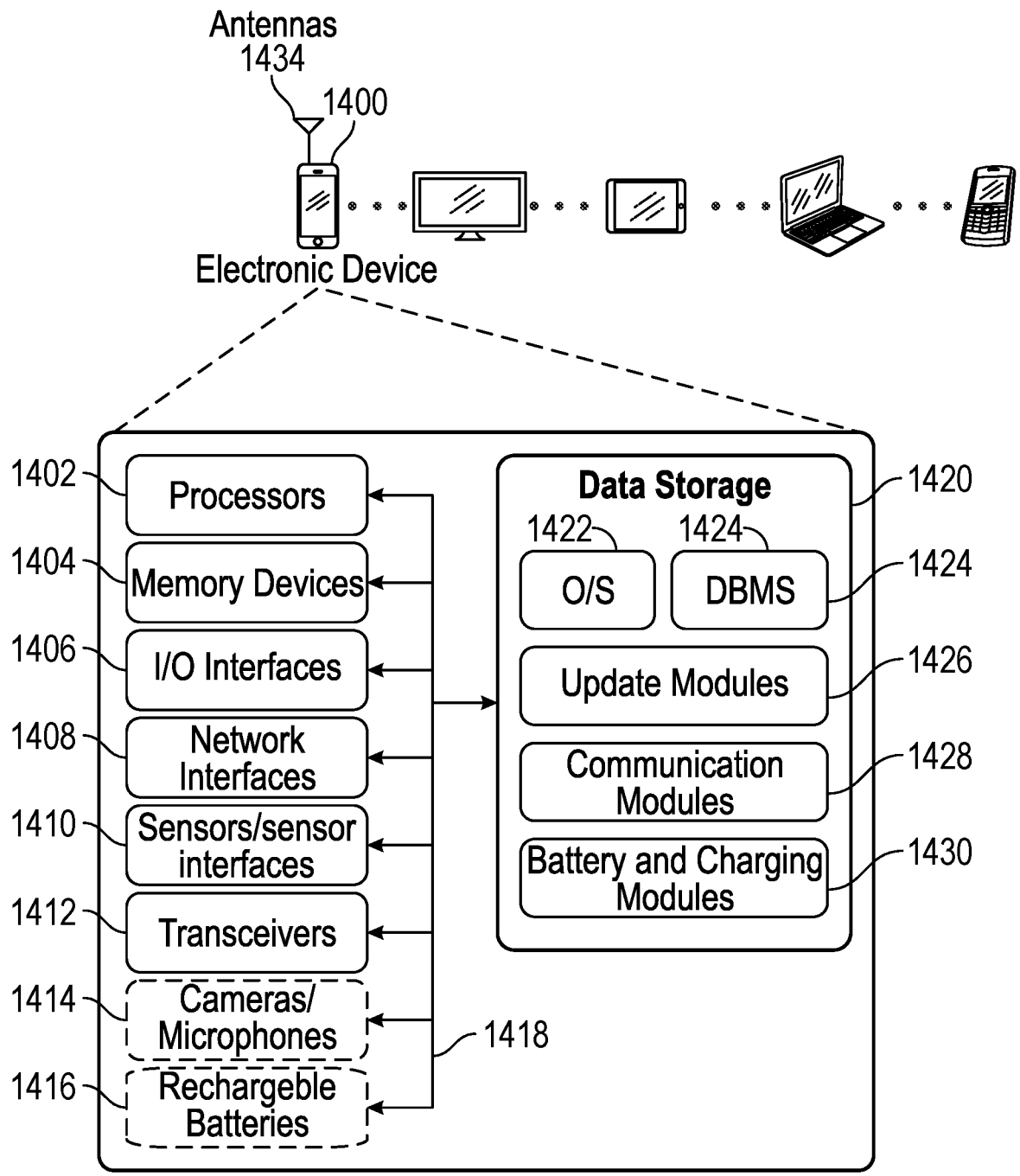
FIG. 14 schematically illustrates an example architecture of an electronic device in accordance with one or more embodiments of the disclosure.

FIG. 14 is a schematic block diagram of one or more illustrative electronic device(s) 1400 in accordance with one or more example embodiments of the disclosure. The electronic device(s) 1400 may control the rapid PCR diagnostic system disclosed herein. The electronic device(s) 1400 may include any suitable computing device including, but not limited to, a server system, a mobile device such as a smartphone, a tablet, an e-reader, a wearable device, or the like; a desktop computer; a laptop computer; a content streaming device; a set-top box; a scanning device; or the like.

The electronic device(s) 1400 may be configured to communicate with one or more servers, user devices, or the like. The electronic device(s) 1400 may be any suitable device, such as a mobile device, and may optionally be configured to determine voice commands, determine wake-word utterances, determine and/or control other devices, and other operations. The electronic device(s) 1400 may be configured to present content, detect sound, output digital content, and other functionality In some embodiments, a single remote server or a single group of remote servers may be configured to perform more than one type of functionality in conjunction with an electronic device.

The electronic device(s) 1400 may be configured to communicate via one or more networks. Such network(s) may include, but are not limited to, any one or more different types of communications networks such as for example, cable networks, public networks (e.g., the Internet), private networks (e.g., frame-relay networks), wireless networks, cellular networks, telephone networks (e.g., a public switched telephone network), or any other suitable private or public packet-switched or circuit-switched networks. Further, such network(s) may have any suitable communication range associated therewith and may include, for example, global networks (e.g., the Internet), metropolitan area networks (MANs), wide area networks (WANs), local area networks (LANs), or personal area networks (PANs). In addition, such network(s) may include communication links and associated networking devices (e.g., link-layer switches, routers, etc.) for transmitting network traffic over any suitable type of medium including, but not limited to, coaxial cable, twisted-pair wire (e.g., twisted-pair copper wire), optical fiber, a hybrid fiber-coaxial (HFC) medium, a microwave medium, a radio frequency communication medium, a satellite communication medium, or any combination thereof.

In an illustrative configuration, the electronic device(s) 1400 may include one or more processors (processor(s)) 1402, one or more memory devices 1404 (also referred to herein as memory 1404), one or more input/output (I/O) interface(s) 1406, one or more network interface(s) 1408, one or more sensor(s) or sensor interface(s) 1410, one or more transceiver(s) 1412, one or more optional camera(s) and/or microphone(s) 1414, one or more optional rechargeable batteries 1416, and data storage 1420. The electronic device(s) 1400 may further include one or more bus(es) 1418 that functionally couple various components of the electronic device(s) 1400. The electronic device(s) 1400 may further include one or more antenna(s) 1434 that may include, without limitation, a cellular antenna for transmitting or receiving signals to/from a cellular network infrastructure, an antenna for transmitting or receiving Wi-Fi signals to/from an access point (AP), a Global Navigation Satellite System (GNSS) antenna for receiving GNSS signals from a GNSS satellite, a Bluetooth antenna for transmitting or receiving Bluetooth signals, a Near Field Communication (NFC) antenna for transmitting or receiving NFC signals, and so forth. These various components will be described in more detail hereinafter.

The bus(es) 1418 may include at least one of a system bus, a memory bus, an address bus, or a message bus, and may permit the exchange of information (e.g., data (including computer-executable code), signaling, etc.) between various components of the electronic device(s). The bus(es) 1418 may include, without limitation, a memory bus or a memory controller, a peripheral bus, an accelerated graphics port, and so forth. The bus(es) 1418 may be associated with any suitable bus architecture including, without limitation, an Industry Standard Architecture (ISA), a Micro Channel Architecture (MCA), an Enhanced ISA (EISA), a Video Electronics Standards Association (VESA) architecture, an Accelerated Graphics Port (AGP) architecture, a Peripheral Component Interconnect (PCI) architecture, a PCI-Express architecture, a Personal Computer Memory Card International Association (PCMCIA) architecture, a Universal Serial Bus (USB) architecture, and so forth.

The memory 1404 of the electronic device(s) 1400 may include volatile memory (memory that maintains its state when supplied with power) such as random access memory (RAM) and/or non-volatile memory (memory that maintains its state even when not supplied with power) such as read-only memory (ROM), flash memory, ferroelectric RAM (FRAM), and so forth. Persistent data storage, as that term is used herein, may include non-volatile memory. In certain example embodiments, volatile memory may enable faster read/write access than non-volatile memory. However, in certain other example embodiments, certain types of non-volatile memory (e.g., FRAM) may enable faster read/write access than certain types of volatile memory.

In various implementations, the memory 1404 may include multiple different types of memory such as various types of static random access memory (SRAM), various types of dynamic random access memory (DRAM), various types of unalterable ROM, and/or writeable variants of ROM such as electrically erasable programmable read-only memory (EEPROM), flash memory, and so forth. The memory 1404 may include main memory as well as various forms of cache memory such as instruction cache(s), data cache(s), translation lookaside buffer(s) (TLBs), and so forth. Further, cache memory, such as a data cache, may be a multi-level cache organized as a hierarchy of one or more cache levels (L1, L2, etc.).

The data storage 1420 may include removable storage and/or non-removable storage, including, but not limited to, magnetic storage, optical disk storage, and/or tape storage. The data storage 1420 may provide non-volatile storage of computer-executable instructions and other data. The memory 1404 and the data storage 1420, removable and/or non-removable, are examples of computer-readable storage media (CRSM) as that term is used herein.

The data storage 1420 may store computer-executable code, instructions, or the like that may be loadable into the memory and executable by the processor(s) 1402 to cause the processor(s) 1402 to perform or initiate various operations. The data storage 1420 may additionally store data that may be copied to the memory 1404 for use by the processor(s) 1402 during the execution of the computer-executable instructions. Moreover, output data generated as a result of execution of the computer-executable instructions by the processor(s) 1402 may be stored initially in the memory 1404 and may ultimately be copied to the data storage 1420 for non-volatile storage.

More specifically, the data storage 1420 may store one or more operating systems (O/S) 1422; one or more database management systems (DBMS) 1424; and one or more program module(s), applications, engines, computer-executable code, scripts, or the like such as, for example, one or more update module(s) 1426, one or more communication module(s) 1428, and/or one or more battery and charging module(s) 1430. Some or all of these module(s) may be sub-module(s). Any of the components depicted as being stored in the data storage 1420 may include any combination of software, firmware, and/or hardware. The software and/or firmware may include computer-executable code, instructions, or the like that may be loaded into the memory 1404 for execution by one or more of the processor(s) 1402. Any of the components depicted as being stored in the data storage 1420 may support functionality described in reference to corresponding components named earlier in this disclosure.

The data storage 1420 may further store various types of data utilized by the components of the electronic device(s) 1400. Any data stored in the data storage 1420 may be loaded into the memory 1404 for use by the processor(s) 1402 in executing computer-executable code. In addition, any data depicted as being stored in the data storage 1420 may potentially be stored in one or more datastore(s) and may be accessed via the DBMS and loaded in the memory 1404 for use by the processor(s) 1402 in executing computer-executable code. The datastore(s) may include, but are not limited to, databases (e.g., relational, object-oriented, etc.), file systems, flat files, distributed datastores in which data is stored on more than one node of a computer network, peer-to-peer network datastores, or the like. In FIG. 14, an example datastore(s) may include, for example, historical data for previously identified products, purchase or order history, user profile information, and/or other information.

The processor(s) 1402 may be configured to access the memory 1404 and execute the computer-executable instructions loaded therein. For example, the processor(s) 1402 may be configured to execute the computer-executable instructions of the various program module(s), applications, engines, or the like of the electronic device(s) 1400 to cause or facilitate various operations to be performed in accordance with one or more embodiments of the disclosure. The processor(s) 1402 may include any suitable processing unit capable of accepting data as input, processing the input data in accordance with stored computer-executable instructions, and generating output data. The processor(s) 1402 may include any type of suitable processing unit including, but not limited to, a central processing unit, a microprocessor, a Reduced Instruction Set Computer (RISC) microprocessor, a Complex Instruction Set Computer (CISC) microprocessor, a microcontroller, an Application-Specific Integrated Circuit (ASIC), a Field-Programmable Gate Array (FPGA), a System-on-a-Chip (SoC), a digital signal processor (DSP), and so forth. Further, the processor(s) 1402 may have any suitable microarchitecture design that includes any number of constituent components such as for example, registers, multiplexers, arithmetic logic units, cache controllers for controlling read/write operations to cache memory, branch predictors, or the like. The microarchitecture design of the processor(s) 1402 may be capable of supporting any of a variety of instruction sets.

Referring now to functionality supported by the various program module(s) depicted in FIG. 14, the update module(s) 1426 may include computer-executable instructions, code, or the like that responsive to execution by one or more of the processor(s) 1402 may perform functions including, but not limited to, requesting and/or receiving software updates, such as over-the-air updates, requesting battery voltage data, storing data, modifying maximum battery charge values at integrated circuits, such as at a Power Management Integrated Circuit, controlling charging schemes and/or charging parameters, and the like.

The communication module(s) 1428 may include computer-executable instructions, code, or the like that are responsive to execution by one or more of the processor(s) 1402 may perform functions including, but not limited to, sending and/or receiving data, including content, sending and/or receiving instructions and commands, and the like.

The battery and charging module(s) 1430 may include computer-executable instructions, code, or the like that responsive to execution by one or more of the processor(s) 1402 may perform functions including, but not limited to, determining a charging voltage or other charging parameter, calculating elapsed time, calculating battery environment values, calculating acceleration or stress factors, calculating deceleration factors, adjusting charging voltages, determining predicted usage, determining voltage and/or temperature data, and the like.

Referring now to other illustrative components depicted as being stored in the data storage 1420, the O/S 1422 may be loaded from the data storage 1420 into the memory 1404 and may provide an interface between other application software executing on the electronic device(s) 1400 and the hardware resources of the electronic device(s) 1400. More specifically, the O/S 1422 may include a set of computer-executable instructions for managing the hardware resources of the electronic device(s) 1400 and for providing common services to other application programs (e.g., managing memory allocation among various application programs). In certain example embodiments, the O/S 1422 may control the execution of the other program module(s). The O/S 1422 may include any operating system now known or which may be developed in the future including, but not limited to, any server operating system, any mainframe operating system, or any other proprietary or non-proprietary operating system.

The DBMS 1424 may be loaded into the memory 1404 and may support functionality for accessing, retrieving, storing, and/or manipulating data stored in the memory 1404 and/or data stored in the data storage 1420. The DBMS 1424 may use any of a variety of database models (e.g., relational model, object model, etc.) and may support any of a variety of query languages. The DBMS 1424 may access data represented in one or more data schemas and stored in any suitable data repository including, but not limited to, databases (e.g., relational, object-oriented, etc.), file systems, flat files, distributed datastores in which data is stored on more than one node of a computer network, peer-to-peer network datastores, or the like. In those example embodiments in which the electronic device(s) 1400 is a mobile device, the DBMS 1424 may be any suitable lightweight DBMS optimized for performance on a mobile device.

Referring now to other illustrative components of the electronic device(s) 1400, the input/output (I/O) interface(s) 1406 may facilitate the receipt of input information by the electronic device(s) 1400 from one or more I/O devices as well as the output of information from the electronic device(s) 1400 to the one or more I/O devices. The I/O devices may include any of a variety of components, such as a display or display screen having a touch surface or touchscreen; an audio output device for producing sound, such as a speaker; an audio capture device, such as a microphone; an image and/or video capture device, such as a camera; a haptic unit; and so forth. Any of these components may be integrated into the electronic device(s) 1400 or may be separate. The I/O devices may further include, for example, any number of peripheral devices such as data storage devices, printing devices, and so forth.

The I/O interface(s) 1406 may also include an interface for an external peripheral device connection such as universal serial bus (USB), FireWire, Thunderbolt, Ethernet port, or other connection protocol that may connect to one or more networks. The I/O interface(s) 1406 may also include a connection to one or more of the antenna(s) 1434 to connect to one or more networks via a wireless local area network (WLAN) (such as Wi-Fi) radio, Bluetooth, ZigBee, and/or a wireless network radio, such as a radio capable of communication with a wireless communication network such as a Long Term Evolution (LTE) network, WiMAX network, 3G network, a ZigBee network, etc.

The electronic device(s) 1400 may further include one or more network interface(s) 2408 via which the electronic device(s) 1400 may communicate with any of a variety of other systems, platforms, networks, devices, and so forth. The network interface(s) 1408 may enable communication, for example, with one or more wireless routers, one or more host servers, one or more web servers, and the like via one or more networks.

The antenna(s) 1434 may include any suitable type of antenna depending, for example, on the communications protocols used to transmit or receive signals via the antenna(s) 1434. Non-limiting examples of suitable antennas may include directional antennas, non-directional antennas, dipole antennas, folded dipole antennas, patch antennas, multiple-input multiple-output (MIMO) antennas, or the like. The antenna(s) 1434 may be communicatively coupled to one or more transceivers 1412 or radio components to which or from which signals may be transmitted or received.

As previously described, the antenna(s) 1434 may include a cellular antenna configured to transmit or receive signals in accordance with established standards and protocols, such as Global System for Mobile Communications (GSM), 3G standards (e.g., Universal Mobile Telecommunications System (UMTS), Wideband Code Division Multiple Access (W-CDMA), CDMA2000, etc.), 4G standards (e.g., Long-Term Evolution (LTE), WiMax, etc.), direct satellite communications, or the like.

The antenna(s) 1434 may additionally, or alternatively, include a Wi-Fi antenna configured to transmit or receive signals in accordance with established standards and protocols, such as the IEEE 802.11 family of standards, including via 2.4 GHz channels (e.g., 802.11b, 802.11g, 802.11n), 5 GHz channels (e.g., 802.11n, 802.11ac), or 60 GHz channels (e.g., 802.11ad). In alternative example embodiments, the antenna(s) 1434 may be configured to transmit or receive radio frequency signals within any suitable frequency range, forming part of the unlicensed portion of the radio spectrum.

The antenna(s) 1434 may additionally, or alternatively, include a GNSS antenna configured to receive GNSS signals from three or more GNSS satellites carrying time-position information to triangulate a position therefrom. Such a GNSS antenna may be configured to receive GNSS signals from any current or planned GNSS such as, for example, the Global Positioning System (GPS), the GLONASS System, the Compass Navigation System, the Galileo System, or the Indian Regional Navigational System.

The transceiver(s) 1412 may include any suitable radio component(s) for—in cooperation with the antenna(s) 1434—transmitting or receiving radio frequency (RF) signals in the bandwidth and/or channels corresponding to the communications protocols utilized by the electronic device(s) 1400 to communicate with other devices. The transceiver(s) 1412 may include hardware, software, and/or firmware for modulating, transmitting, or receiving—potentially in cooperation with any of antenna(s) 1434—communications signals according to any of the communications protocols discussed above including, but not limited to, one or more Wi-Fi and/or Wi-Fi direct protocols, as standardized by the IEEE 802.11 standards, one or more non-Wi-Fi protocols, or one or more cellular communications protocols or standards. The transceiver(s) 1412 may further include hardware, firmware, or software for receiving GNSS signals. The transceiver(s) 1412 may include any known receiver and baseband suitable for communicating via the communications protocols utilized by the electronic device(s) 1400. The transceiver(s) 1412 may further include a low noise amplifier (LNA), additional signal amplifiers, an analog-to-digital (A/D) converter, one or more buffers, a digital baseband, or the like.

The sensor(s)/sensor interface(s) 1410 may include or may be capable of interfacing with any suitable type of sensing device such as, for example, inertial sensors, force sensors, thermal sensors, photocells, and so forth. Example types of inertial sensors may include accelerometers (e.g., MEMS-based accelerometers), gyroscopes, and so forth.

The camera(s) 1414 may be any device configured to capture ambient light or images. The microphone(s) 1414 may be any device configured to receive analog sound input or voice data. The rechargeable battery (or batteries) 1416 may be any suitable power storage device, such as a lithium-ion battery, and may be in various form factors, such as pouch form factors, cylindrical form factors, and the like.

It should be appreciated that the program module(s), applications, computer-executable instructions, code, or the like depicted in FIG. 14 as being stored in the data storage 1420 are merely illustrative and not exhaustive and that processing described as being supported by any particular module may alternatively be distributed across multiple module(s) or performed by a different module. In addition, various program module(s), script(s), plug-in(s), Application Programming Interface(s) (API(s)), or any other suitable computer-executable code hosted locally on the electronic device(s) 1400, and/or hosted on other computing device(s) accessible via one or more networks, may be provided to support functionality provided by the program module(s), applications, or computer-executable code depicted in FIG. 14 and/or additional or alternate functionality. Further, functionality may be modularized differently such that processing described as being supported collectively by the collection of program module(s) depicted in FIG. 14 may be performed by a fewer or greater number of module(s), or functionality described as being supported by any particular module may be supported, at least in part, by another module. In addition, program module(s) that support the functionality described herein may form part of one or more applications executable across any number of systems or devices in accordance with any suitable computing model such as, for example, a client-server model, a peer-to-peer model, and so forth. In addition, any of the functionality described as being supported by any of the program module(s) depicted in FIG. 14 may be implemented, at least partially, in hardware and/or firmware across any number of devices.

It should further be appreciated that the electronic device(s) 1400 may include alternate and/or additional hardware, software, or firmware components beyond those described or depicted without departing from the scope of the disclosure. More particularly, it should be appreciated that software, firmware, or hardware components depicted as forming part of the electronic device(s) 1400 are merely illustrative and that some components may not be present or additional components may be provided in various embodiments. While various illustrative program module(s) have been depicted and described as software module(s) stored in the data storage 1420, it should be appreciated that functionality described as being supported by the program module(s) may be enabled by any combination of hardware, software, and/or firmware. It should further be appreciated that each of the above-mentioned module(s) may, in various embodiments, represent a logical partitioning of supported functionality. This logical partitioning is depicted for ease of explanation of the functionality and may not be representative of the structure of software, hardware, and/or firmware for implementing the functionality. Accordingly, it should be appreciated that functionality described as being provided by a particular module may, in various embodiments, be provided at least in part by one or more other module(s). Further, one or more depicted module(s) may not be present in certain embodiments, while in other embodiments, additional module(s) not depicted may be present and may support at least a portion of the described functionality and/or additional functionality. Moreover, while certain module(s) may be depicted and described as sub-module(s) of another module, in certain embodiments, such module(s) may be provided as independent module(s) or as sub-module(s) of other module(s).

Program module(s), applications, or the like disclosed herein may include one or more software components including, for example, software objects, methods, data structures, or the like. Each such software component may include computer-executable instructions that, responsive to execution, cause at least a portion of the functionality described herein (e.g., one or more operations of the illustrative methods described herein) to be performed.

A software component may be coded in any of a variety of programming languages. An illustrative programming language may be a lower-level programming language, such as an assembly language associated with a particular hardware architecture and/or operating system platform. A software component comprising assembly language instructions may require conversion into executable machine code by an assembler prior to execution by the hardware architecture and/or platform.

Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, or a report writing language. In one or more example embodiments, a software component comprising instructions in one of the foregoing examples of programming languages may be executed directly by an operating system or other software component without having to be first transformed into another form.

A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

Software components may invoke or be invoked by other software components through any of a wide variety of mechanisms. Invoked or invoking software components may comprise other custom-developed application software, operating system functionality (e.g., device drivers, data storage (e.g., file management) routines, other common routines, and services, etc.), or third-party software components (e.g., middleware, encryption, or other security software, database management software, file transfer or other network communication software, mathematical or statistical software, image processing software, and format translation software).

Software components associated with a particular solution or system may reside and be executed on a single platform or may be distributed across multiple platforms. The multiple platforms may be associated with more than one hardware vendor, underlying chip technology, or operating system. Furthermore, software components associated with a particular solution or system may be initially written in one or more programming languages, but may invoke software components written in another programming language.

Computer-executable program instructions may be loaded onto a special-purpose computer or other particular machine, a processor, or other programmable data processing apparatus to produce a particular machine, such that execution of the instructions on the computer, processor, or other programmable data processing apparatus causes one or more functions or operations specified in the flow diagrams to be performed. These computer program instructions may also be stored in a computer-readable storage medium (CRSM) that upon execution may direct a computer or other programmable data processing apparatus to function in a particular manner, such that the instructions stored in the computer-readable storage medium produce an article of manufacture including instruction means that implement one or more functions or operations specified in the flow diagrams. The computer program instructions may also be loaded onto a computer or other programmable data processing apparatus to cause a series of operational elements or steps to be performed on the computer or other programmable apparatus to produce a computer-implemented process.

Additional types of CRSM that may be present in any of the devices described herein may include, but are not limited to, programmable random access memory (PRAM), SRAM, DRAM, RAM, ROM, electrically erasable programmable read-only memory (EEPROM), flash memory or other memory technology, compact disc read-only memory (CD-ROM), digital versatile disc (DVD) or other optical storage, magnetic cassettes, magnetic tape, magnetic disk storage or other magnetic storage devices, or any other medium which can be used to store the information and which can be accessed. Combinations of any of the above are also included within the scope of CRSM. Alternatively, computer-readable communication media (CRCM) may include computer-readable instructions, program module(s), or other data transmitted within a data signal, such as a carrier wave, or other transmission. However, as used herein, CRSM does not include CRCM.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

That which is claimed is:

1. A sample collection device for use in PCR testing comprising:
   a swab stick which comprises a plunger handle and a saliva swab extending from the plunger handle; and
   a sample container configured to receive the saliva swab therein following collection of a saliva specimen, wherein the sample container comprises:
   a swab chamber for receiving the saliva swab;
   a bulk saliva collection chamber in fluid communication with the swab chamber, the bulk saliva collection chamber being configured to receive saliva transferred from the saliva swab;
   a micro sample chamber in fluid communication with the bulk saliva collection chamber, the micro sample chamber being configured to hold a selected volume of the saliva; and
   a metering piston with a piercing tip,
   wherein the sample container is configured to (i) be releasably attached to a PCR sample tube, which contains a lyophilized master mix, (ii) pierce a seal on the PCR sample tube, and (iii) meter the selected volume of the saliva from the micro sample chamber into the PCR sample tube.

2. The sample collection device for use in PCR testing comprising:
   a swab stick which comprises a plunger handle and a saliva swab extending from the plunger handle; and a sample container configured to receive the saliva swab therein following collection of a saliva specimen, wherein the sample container comprises:
a swab chamber for receiving the saliva swab;
a bulk saliva collection chamber in fluid communication with the swab chamber, the bulk saliva collection chamber being configured to receive saliva transferred from the saliva swab;
a micro sample chamber in fluid communication with the bulk saliva collection chamber, the micro sample chamber being configured to hold a selected volume of the saliva; and
a metering piston with a piercing tip,
wherein the sample container is configured to (i) be releasably attached to a PCR sample tube, which contains a lyophilized master mix, (ii) pierce a seal on the PCR sample tube, and (iii) meter the selected volume of the saliva from the micro sample chamber into the PCR sample tube, and
wherein the swab chamber, the bulk saliva collection chamber, and the micro sample chamber are aligned in series along a common axis within the sample container, and the swab stick further comprises a swab plunger configured to translate into the bulk saliva collection chamber along the axis to contact the metering piston to push the metering piston into the micro sample chamber and displace the selected volume of the saliva from the micro sample chamber into the PCR sample tube.

3. A sample collection device comprising:
a swab configured to hold a biological sample; and
a sample container configured to receive the swab and enable transfer of a first portion of the biological sample to a first chamber of the sample container,
wherein the sample container is configured to enable transfer of a second portion of the biological sample from the first chamber into a PCR sample tube that is releasably attached to the sample container,
wherein the swab comprises a handle end portion and an opposing end portion which comprises an absorbent swab material, and a sealing member is disposed between the handle end portion and the absorbent swab material, the sealing member being configured to engage with an interior surface of a swab receiving chamber of the sample container, and
wherein the sample container further comprises a metering piston configured to be translated within the first chamber and transfer the second portion of the biological sample into the PCR sample tube.

4. The sample collection device of claim 3, wherein the swab comprises an absorbent swab material, and wherein the sample container is configured to cause the absorbent swab material to be compressed to release the first portion of the biological sample into the first chamber.

5. The sample collection device of claim 3, wherein the sample container comprises an elongated body having a first end for receiving the swab and having an opposing second end configured for releasably attaching to the PCR sample tube.

6. The sample collection device of claim 3, wherein the sample container further comprises a second chamber in fluid communication with the first chamber, wherein the second chamber is configured to hold at least 5 µl of the biological sample.

7. A sample collection device comprising:
a swab configured to hold a biological sample; and
a sample container configured to receive the swab and transfer a first portion of the biological sample to a first chamber of the sample container; and
a PCR sample tube releasably attached to the sample container,
wherein the sample container further comprises (i) a swab chamber which has a first opening configured to receive the swab therethrough and an opposed second opening in fluid communication with the first chamber, and (ii) a metering piston located within the first chamber and configured to displace a second portion of the biological sample from the first chamber into the PCR sample tube by translation of the metering piston within the first chamber.

8. The sample collection device of claim 7, wherein the swab comprises an absorbent swab material configured to be compressed by the sample container to release the first portion of the biological sample into the first chamber.

9. The sample collection device of claim 7, wherein swab comprises:
a handle end portion,
an opposing end portion which comprises an absorbent swab material, and
a sealing member disposed between the handle end portion and the absorbent swab material,
wherein the sealing member is configured to engage with an interior surface of a swab receiving chamber of the sample container.

10. The sample collection device of claim 7, wherein the metering piston is configured to translate through a piston channel in the sample container and into a second chamber in fluid communication with the first chamber to transfer the second portion of the biological sample from the first chamber into the PCR sample tube.

11. The sample collection device of claim 10, wherein the metering piston comprises a piercing tip oriented toward the PCR sample tube.

12. The sample collection device of claim 7, wherein the sample container comprises an elongated body having a first end for receiving the swab and having an opposing second end to which the PCR sample tube is releasably attached.

13. The sample collection device of claim 7, wherein the sample container further comprises a second chamber in fluid communication with the first chamber, wherein the second chamber is configured to hold at least 5 µl of the biological sample.

14. The sample collection device of claim 7, wherein the PCR sample tube contains a lyophilized master mix.

15. The sample collection device of claim 7, wherein the sample container further comprises a projection configured to pierce a seal on a top of the PCR sample tube upon attachment of the PCR sample tube to the sample container.

16. The sample collection device of claim 7, wherein:
the sample container further comprises a swab chamber configured to receive the swab; and
the swab chamber, the first chamber, and a micro sample chamber are aligned in series along a common axis within the sample container.

17. The sample collection device of claim 7, wherein the metering piston is located entirely within the first chamber.

18. The sample collection device of claim 7, wherein the translation of the metering piston displaces the second portion of the biological sample directly into the PCR sample tube.

19. A sample collection device comprising:
a swab configured to hold a biological sample; and
a sample container configured to receive the swab and transfer a first portion of the biological sample to a first chamber of the sample container; and
a PCR sample tube releasably attached to the sample container,
wherein:
the sample container further comprises a swab chamber configured to receive the swab;
the swab chamber, the first chamber, and a micro sample chamber are aligned in series along a common axis within the sample container;
the sample container further comprises a metering piston; and
the swab further comprises a swab plunger configured to translate into first chamber along the common axis to contact the metering piston to push the metering piston into the micro sample chamber and displace a selected volume of the biological sample from the micro sample chamber into the PCR sample tube.

* * * * *

UNITED STATES PATENT AND TRADEMARK OFFICE
CERTIFICATE OF CORRECTION

PATENT NO. : 12,090,483 B2
APPLICATION NO. : 17/703570
DATED : September 17, 2024
INVENTOR(S) : Jasmin B. Farshi et al.

It is certified that error appears in the above-identified patent and that said Letters Patent is hereby corrected as shown below:

In the Claims

Claim 2 at Column 22, Line 64 should read:
-- A sample collection device for use in PCR testing --.

Claim 2 at Column 23, Line 25 should read:
-- collection chamber along the common axis to contact the metering --.

Signed and Sealed this
Twelfth Day of November, 2024

Katherine Kelly Vidal
*Director of the United States Patent and Trademark Office*